US008160264B2

(12) United States Patent
Itou et al.

(10) Patent No.: US 8,160,264 B2
(45) Date of Patent: Apr. 17, 2012

(54) TRANSFER FUNCTION ESTIMATING DEVICE, NOISE SUPPRESSING APPARATUS AND TRANSFER FUNCTION ESTIMATING METHOD

(75) Inventors: Taisuke Itou, Kawasaki (JP); Naoshi Matsuo, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 530 days.

(21) Appl. No.: 12/453,177

(22) Filed: Apr. 30, 2009

(65) Prior Publication Data

US 2010/0027805 A1 Feb. 4, 2010

(30) Foreign Application Priority Data

Jul. 30, 2008 (JP) ................................ 2008-196943

(51) Int. Cl.
*A61F 11/06* (2006.01)
*G10K 11/16* (2006.01)

(52) U.S. Cl. .................................................... 381/71.12

(58) Field of Classification Search ................. 381/71.1, 381/71.8, 71.12
See application file for complete search history.

(56) References Cited

U.S. PATENT DOCUMENTS

| | | | | |
|---|---|---|---|---|
| 5,267,320 | A | 11/1993 | Fukumizu | |
| 5,987,144 | A | 11/1999 | Carme et al. | |
| 6,208,477 | B1 * | 3/2001 | Cloke et al. | 360/31 |
| 6,862,356 | B1 | 3/2005 | Makino | |
| 2003/0086573 | A1 | 5/2003 | Schobben et al. | |
| 2005/0053244 | A1 | 3/2005 | Onishi et al. | |

FOREIGN PATENT DOCUMENTS

| | | | |
|---|---|---|---|
| DE | 10028557 | A1 | 12/2000 |
| EP | 0 285 632 | B1 | 6/1993 |
| EP | 1 515 304 | A2 | 3/2005 |
| JP | 1-501344 | | 5/1989 |
| JP | 3-44299 | | 2/1991 |
| JP | 5-11771 | | 1/1993 |
| JP | 2001-57699 | | 2/2001 |
| JP | 2005-84500 | | 3/2005 |
| JP | 2007-158731 | | 6/2007 |
| WO | 88/02912 | | 4/1988 |

OTHER PUBLICATIONS

European Search Report mailed Dec. 23, 2009 in corresponding European Patent Application 09159108.1.

* cited by examiner

*Primary Examiner* — David Mis
(74) *Attorney, Agent, or Firm* — Staas & Halsey LLP

(57) ABSTRACT

A transfer function estimating device for estimating a transfer function of a sound, includes: a sound receiving module receiving a sound from a given sound source and converting the sound into a tone signal; a storage module storing first transfer functions of the sound propagating from the given sound source to the sound receiving module and transformation coefficients for converting the first transfer functions into given second transfer functions so as to associate with each other; a reference tone signal acquiring module acquiring a reference tone signal of the sound source; an acquiring module acquiring a transfer function of the sound received by the sound receiving module on the basis of the tone signal and the reference tone signal; a specifying module acquiring a cross-correlation value between the transfer function acquired by the acquiring module and each of the first transfer functions stored in the storage module.

20 Claims, 19 Drawing Sheets

F I G. 3

| IDENTIFICATION NUMBER | IMPULSE RESPONSE Il(t) | IMPULSE RESPONSE Ir(t) | TRANSFORM MATRIX Ts |
|---|---|---|---|
| 1 | IlA(t) | IrA(t) | TsA |
| 2 | IlB(t) | IrB(t) | TsB |
| 3 | IlC(t) | IrC(t) | TsC |
| ⋮ | ⋮ | ⋮ | ⋮ |

TRANSFER FUNCTION ESTIMATING DEVICE, NOISE SUPPRESSING APPARATUS AND TRANSFER FUNCTION ESTIMATING METHOD

CROSS-REFERENCE OF RELATED APPLICATION

This application is based upon and claims the benefit of priority of the prior Japanese Patent Application No. 2008-196943, filed on Jul. 30, 2008, the entire contents of which are incorporated herein by reference.

FIELD

The embodiments discussed herein relate to a transfer function estimating device, a noise suppressing apparatus equipped with the transfer function estimating device, and a transfer function estimating method, which accurately estimate transfer functions of sound propagated from a given sound source to any listening point.

BACKGROUND

There have been discussed noise suppressing apparatuses like an active noise controller which suppresses a noise by generating such sounds that it cancels out the noise when the noise occurs (for example, refer to Japanese Laid-Open Patent Publication No. 2001-057699, Japanese Laid-Open Patent Publication No. 1991(H03)-044299, and Japanese Laid-Open Patent Publication No. 1993(H05)-011771). FIG. 19 is a schematic view of a configuration example of a noise suppressing apparatus of related art. Incidentally, FIG. 19 shows a view in which the noise suppressing apparatus and a listener are viewed from above, and the listener faces towards the upper part of FIG. 19.

The noise suppressing apparatus illustrated in FIG. 19 includes a noise source 101, a loud speaker to output a canceling sound for canceling out the noise, an error microphone 103 provided in the vicinity of the listener, a reference microphone 104 to receive the sound (noise) from the noise source 101 and convert it to a tone signal, a canceling sound generating module 105 and the like.

The noise suppressing apparatus of the configuration described above finds transfer functions of sound (noise) between the noise source 101 and the error microphone 103 in the canceling sound generating module 105 on the basis of the tone signals received by the reference microphone 104 and the tone signals received by the error microphone 103. The noise suppressing apparatus also generates the canceling sound such that the sound (noise) received by the error microphone 103 is made into a minimum on the basis of the transfer functions found in the canceling sound generating module 105, and outputs the canceling sound generated from the loud speaker 102.

SUMMARY

According to an aspect of the invention, a transfer function estimating device, for estimating a transfer function of a sound, includes: a sound receiving module receiving a sound from a given sound source and converting the sound into a tone signal; a storage module storing first transfer functions of the sound propagating from the given sound source to the sound receiving module and transformation coefficients for converting the first transfer functions into given second transfer functions so as to associate with each other; a reference tone signal acquiring module acquiring a reference tone signal of the sound source; an acquiring module acquiring a transfer function of the sound received by the sound receiving module on the basis of the tone signal and the reference tone signal; a specifying module acquiring a cross-correlation value between the transfer function acquired by the acquiring module and each of the first transfer functions stored in the storage module, and specifying the first transfer function indicating the highest cross-correlation value; a read-out module reading out the transformation coefficient corresponding to the first transfer function specified by the specifying module from the storage module; and an estimating module estimating the second transfer function corresponding to the transfer function acquired by the acquiring module using the transformation coefficient read out by the read-out module.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 3 is a schematic view illustrating an example of contents registered in a transform matrix table;

DESCRIPTION OF EMBODIMENTS

The noise suppressing apparatus including a configuration as described above performs a control such that the noise is made into a minimum at a position of the error microphone 103. If the actual listening point (ears of the listener) is apart from the error microphone 103, since the sound transfer functions between the noise source 101 and the error microphone 103 becomes different considerably from the sound transfer functions between the noise source 101 and the listening point, it becomes difficult to control the noise at the listening point. Specifically, for example, it has been confirmed by an experiment that if the listening point is apart from the error microphone 103 by 10 cm, the suppressed noise amount reduces by 5 dB. Therefore, it is desired that the error microphone 103 is set at the position of the ears of a listener (user), that is, the actual listening point.

However, the position of the listening point is not fixed due to the movement of the listener, differences of the somatotype of plural listeners and the like, and the position to arrange the error microphone 103 is limited in a place such as a vehicle. Thus, it is difficult to set the error microphone 103 accurately at the position of the listening point.

Therefore, there is required that the sound transfer function between the noise source 101 and the listening point can be estimated accurately even if the error microphone 103 is set at a position apart from the listening point, and the position of the listening point varies.

Hereinafter, a transfer function estimating device will be described in detail on the basis of the drawings illustrating embodiments applied to a car audio system. Incidentally, in the following embodiments the configuration is such which music and audio outputted from the car audio system are suppressed as the noise at a given area using the transfer functions estimated by the transfer function estimating device. The transfer function estimating device, the transfer function estimating method and a computer program disclosed in the present application are used in the noise suppressing apparatus applied to the car audio system, as well as can be applied to various devices which perform an estimation of the sound transfer functions at a position different from the actual observation position and conducts various processes using the estimated transfer functions.

Specifically, for example, when the transfer function estimating device is installed in a hall such as a concert hall or a dance hall, or a room provided with a home theater system to simulate how the sound is listened at individual auditorium seats, the transfer function estimating device can be used. Further, when the transfer function estimating device is installed in a room to detect a position of a given sound source and a movement of the sound source in the room, the transfer function estimating device can be used.

Embodiment 1

Figure 1:
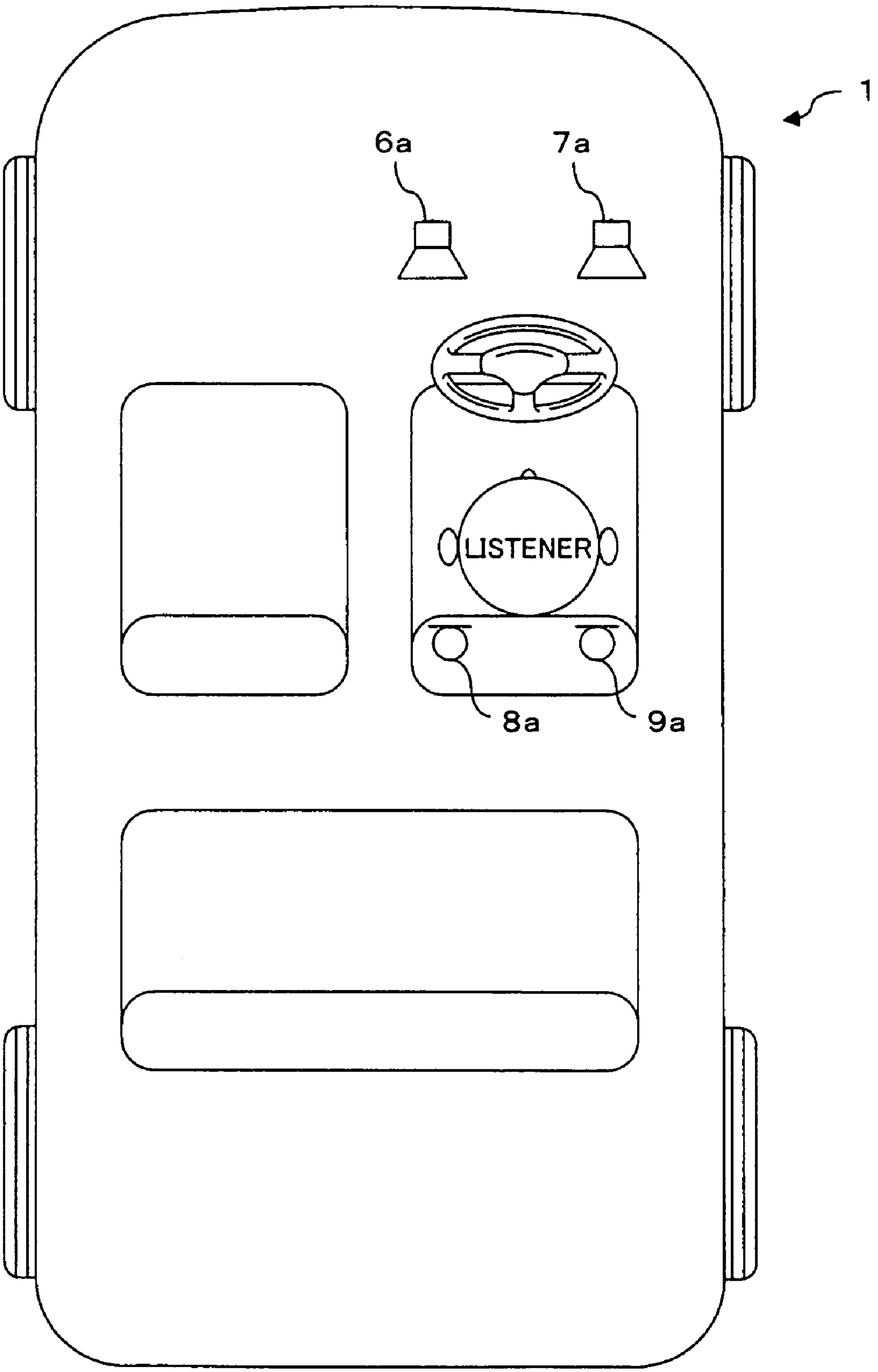
FIG. 1 is a schematic view illustrating an installation example of a car audio system of Embodiment 1.

Hereinafter, a car audio system according to Embodiment 1 will be described. FIG. 1 is a schematic view illustrating an installation example of a car audio system of Embodiment 1. In the car audio system 1 of Embodiment 1, a sound source loud speaker 6*a* outputting an audio signal, and a canceling sound loud speaker 7*a* outputting canceling sounds for canceling music and audio on the basis of the audio signal are installed in an appropriate location in a car dashboard in front of the driver (listener). Further in the car audio system 1 according to Embodiment 1, two error microphones 8*a* and 9*a* are provided at appropriate locations on the ceiling above a driver's seat or at locations near driver's ears in a head rest of a driver's seat. A body of the car audio system 1 is installed, for example, under the seat(s), and the sound source loud speaker 6*a*, the canceling sound loud speaker 7*a*, and the error microphones 8*a* and 9*a* are coupled with the body of the car audio system 1 via a cable, for example. Incidentally, individual installation positions of the sound source loud speaker 6*a*, the canceling sound loud speaker 7*a*, and the error microphones 8*a* and 9*a* are not limited to the example illustrated in FIG. 1.

The car audio system 1 according to Embodiment 1 suppresses the level of music which is outputted from the sound source loud speaker 6*a* and listened by the driver (the listener) by outputting the generated canceling sound from the canceling sound loud speaker 7*a*. Further, the car audio system 1 according to Embodiment 1 estimates the transfer functions of the sound outputted from the sound source loud speaker 6*a*, the characteristics representing how the sound is heard at the position of the ears of the listener (i.e., to what kind of sound the sound changes) on the basis of the transfer functions of the sound outputted from the sound source loud speaker 6*a* at the installation position of the error microphones 8*a* and 9*a*. Then, the car audio system 1 according to Embodiment 1 generates a canceling sound such that the sound outputted from the sound source loud speaker 6*a* is suppressed at the position of the ears of the listener on the basis of the estimated transfer functions.

Incidentally, it is possible that the car audio system 1 according to Embodiment 1 is installed on the side of a passenger seat to suppress the level of music which is outputted from the sound source loud speaker 6*a* and listened by the person in the passenger seat. The noise suppressing apparatus utilizing the transfer function estimating device disclosed in the present application is not limited to the configuration where music actually outputted from the sound source loud speaker 6*a* is suppressed, but can suppress a noise generated in the vehicle (engine sound, sound outputted from a car navigation system, etc.), for example.

Figure 2:
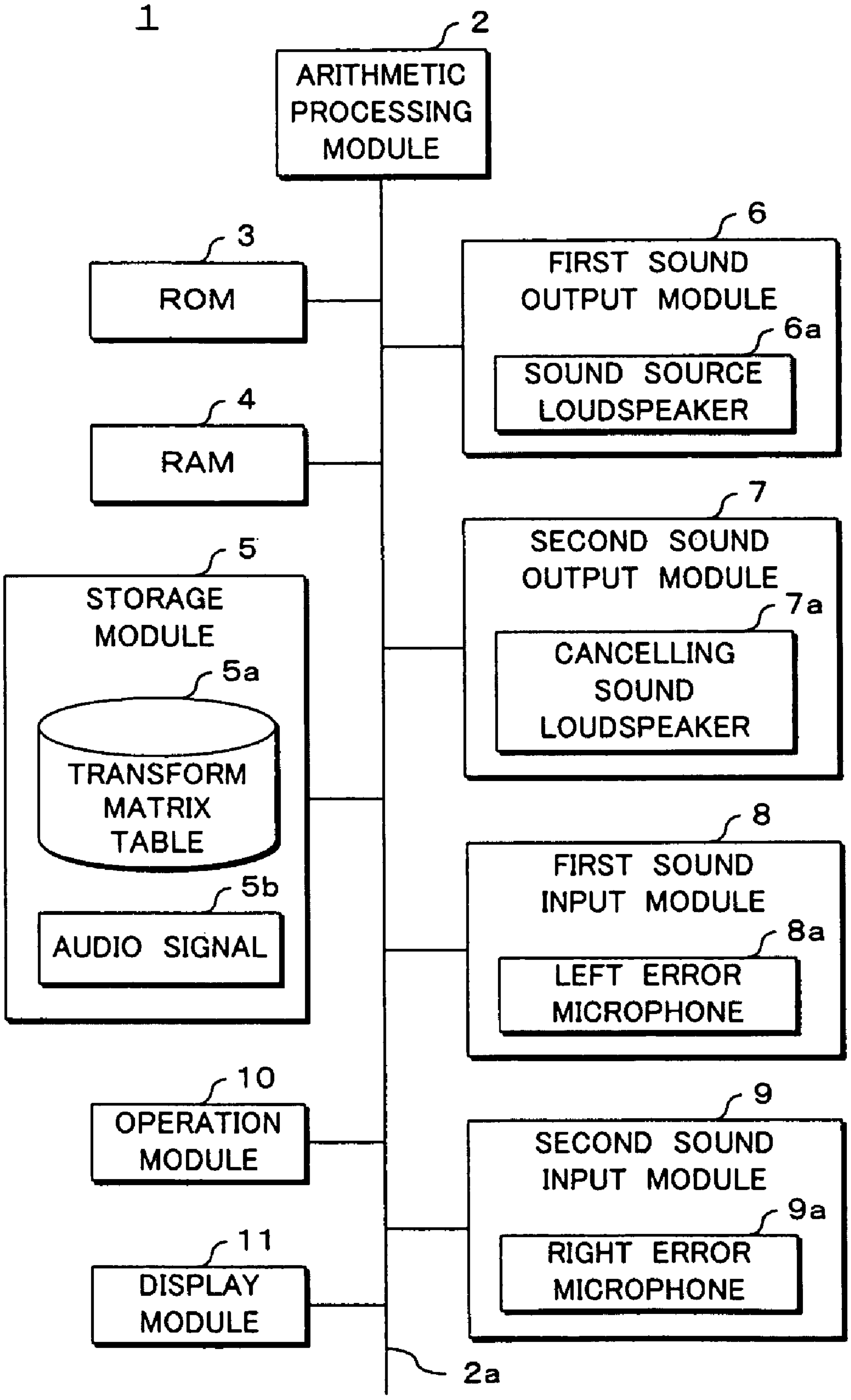
FIG. 2 is a block diagram illustrating an example of a configuration of the car audio system according to Embodiment 1.

Referring to FIG. 2, the car audio system 1 according to Embodiment 1 includes an arithmetic processing module 2, a ROM (Read Only Memory) 3, a RAM (Random Access Memory) 4, a storage module 5, the first sound output module 6, the second sound output module 7, the first sound input module 8, the second sound input module 9, an operation module 10, a display module 11 and the like. The hardware described above is each coupled with each other via a bus 2*a*.

The arithmetic processing module 2 is a CPU (Central Processing Unit), an MPU (Micro Processor Unit) or the like, and controls each of the hardware described above, and reads a control program stored in the ROM 3 in advance into the RAM 4 at an appropriate timing to execute thereof. The ROM 3 stores therein various control programs in advance, which are necessary for operating the car audio system 1. The RAM 4 is an SRAM, a flash memory or the like, and stores temporarily therein various data generated when the arithmetic processing module 2 is executing the control program.

The storage module 5 is a flash memory, for example, and stores therein various control programs necessary for operating the car audio system 1, a transform matrix table (the storage module) 5*a* as illustrated in FIG. 3, various audio signals 5*b* and the like. The audio signal 5*b* does not have to be included in the storage module 5, but may be read out of a recording medium such as a CD-R (Compact Disc Recordable) in which the audio signals are recorded by setting the recording medium.

As illustrated in FIG. 3, registered in the transform matrix table 5*a* are the transfer functions (first transfer functions) Il(t) and Ir(t) at two positions respectively corresponding to the ears of a person, and a transformation coefficient Ts to transform these transfer functions into given transfer functions (second transfer functions), in plural numbers, in a state where these transfer functions are associated with an identification number respectively for identifying each of them. The first transfer functions are found for the number of sound receiving modules (error microphones 8*a* and 9*a*). That is, in the case of a human, the sound receiving module corresponds to the ears, thus, two sound receiving modules are provided. Incidentally, in Embodiment 1, an impulse response is found for use as the transfer function, and a transform matrix of 2×2 is used as the transformation coefficient Ts.

In the car audio system 1 according to Embodiment 1, stored in the car audio system 1 is, for example, the transform matrix table 5*a* generated by a generating process of the transform matrix table 5*a* or the transform matrix table 5*a* generated in advance before factory shipment of the car audio system 1 or before factory shipment of the vehicle installed with the car audio system 1. Therefore, when the car audio system 1 or the vehicle installed with the car audio system 1 is brought to the user (driver), the storage module 5 of the car audio system 1 has the transform matrix table 5*a* stored therein.

The first sound output module 6 has the sound source loud speaker 6*a* outputting the sound, a digital/analog converter, an amplifier (both not illustrated) and the like. The second sound output module 7 has the canceling sound loud speaker 7*a* outputting the sound, a digital/analog converter, an amplifier (both not illustrated) and the like. The sound output modules 6 and 7 convert digital tone signals to be audio-outputted into analog tone signals by the digital/analog converters in accordance with instructions from the arithmetic processing module 2, and thereafter, amplifies the signals by the amplifier, and outputs the sound on the basis of the amplified tone signals from the loud speakers 6*a* and 7*a*.

Figure 4:
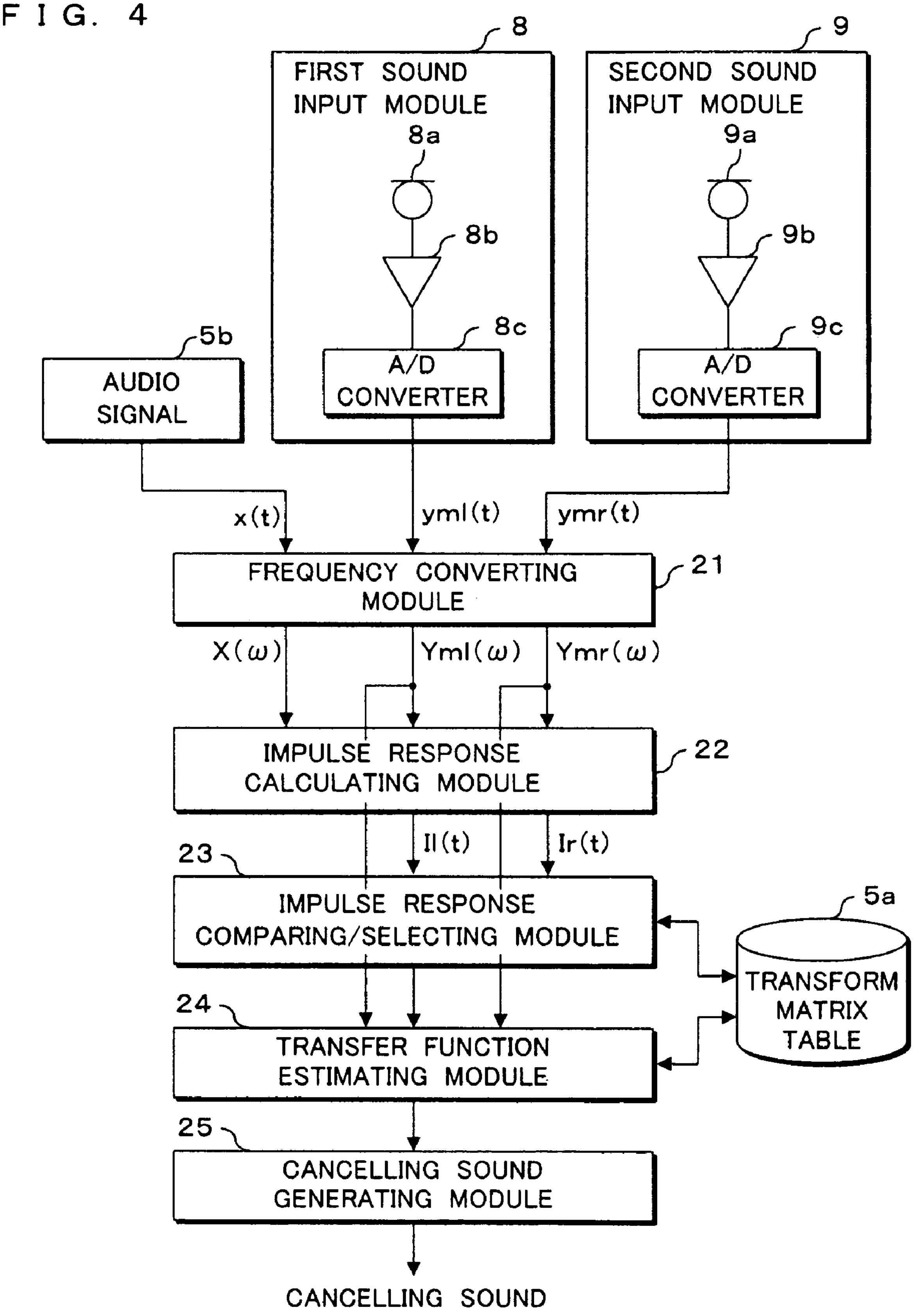
FIG. 4 is a functional block diagram illustrating an example of a functional configuration of the car audio system according to Embodiment 1.

The first sound input module (sound receiving module) 8 has, as illustrated in FIG. 4, the left side error microphone 8*a*, the amplifier 8*b* and the analog/digital converter (hereinafter, referred to as A/D converter) 8*c*. The second sound input module (sound receiving module) 9 has, as illustrated in FIG. 4, the right side error microphone 9*a*, the amplifier 9*b* and the A/D converter 9*c*. Incidentally, provided at the positions in the vicinity of both ears of the listener are, that is, the left side error microphone 8*a* on the left side of the listener as illustrated in FIG. 1, and the right side error microphone 9*a* on the right side of the listener as illustrated in FIG. 1.

The error microphones 8*a* and 9*a* are capacitor microphones, for example, and generate the analog tone signals on the basis of the received sounds and send out the generated tone signals to the amplifiers 8*b* and 9*b*, respectively. The amplifiers 8*b* and 9*b* are gain amplifiers, for example, and amplify the tone signals inputted from the microphones 8*a* and 9*a* and send out the resultant tone signals to the A/D converters 8*c* and 9*c*, respectively. The A/D converters 8*c* and 9*c* convert the tone signals inputted from the amplifiers 8*b* and 9*b* into the digital tone signals by sampling with a given sampling frequency using a filter such as a Low Pass Filter (LPF). The first sound input module 8 and the second sound input module 9 send out the digital tone signals obtained by the A/D converters 8*c* and 9*c* to given output destinations, respectively.

The operation module 10 includes various operation keys necessary for the user to operate the car audio system 1. When the user operates each of the operation keys, the operation module 10 sends out a control signal corresponding to the operated operation key to the arithmetic processing module 2, and the arithmetic processing module 2 then executes a process corresponding to the control signal received from the operation module 10.

The display module 11 is a liquid crystal display (LCD), for example, and displays operating conditions of the car audio system 1, information to be notified to the user and the like in accordance with the instruction from the arithmetic processing module 2.

Hereinafter, described is a function of the car audio system 1 implemented in the car audio system 1 including the above described configuration by the arithmetic processing module 2 executing the various control program stored in the ROM 3. Referring to FIG. 4, in the car audio system 1 according to Embodiment 1, the arithmetic processing module 2 implements each of functions of a frequency converting module 21, an impulse response calculating module 22, an impulse response comparing/selecting module 23, a transfer function estimating module 24, a canceling sound generating module 25 and the like by executing the control program stored in the ROM 3.

Incidentally, the individual functions described above are not limited to the configuration where the function is implemented by the arithmetic processing module 2 executing the control program stored in the ROM 3. For example, the individual functions described above may be implemented by a Digital Signal Processor (DSP) storing computer programs and various data disclosed in the present application incorporated therein.

The first sound input module 8 and the second sound input module 9 respectively send out the tone signals yml(t) and ymr(t) obtained by receiving the sounds to the frequency converting module 21, together with x(t) which is the audio signal (reference tone signal) 5*b* being outputted from the car audio system 1. Note that t is the number of samples, and representing that yml(t) and ymr(t) are the signals sampled with a given sampling frequency. In Embodiment 1, since description is given using as an example of a configuration where the car audio system 1 performs a process of suppressing the music outputted from the sound source loud speaker 6*a*, the first sound input module 8 and the second sound input module 9 are assumed to receive the sounds from the sound source loud speaker 6*a* (given sound source). When the impulse response is found on the basis of the tone signals yml(t) and ymr(t) obtained respectively by the first sound input module 8 and the second sound input module 9 receiving, a change in the head position of the user can be found. Embodiment 1 deals with a case where the noise is the audio signal and the reference tone signal is acquired as the digital signal as it is; however, in a case in which the noise is the engine sound or the like, the reference tone signals may be acquired using a reference microphone.

The frequency converting module 21 is inputted with x(t) representing the audio signal 5*b* which is stored in the storage module 5 and is being outputted from the sound source loud speaker 6*a*, in addition to the tone signals yml(t) and ymr(t) from the first sound input module 8 and the second sound input module 9. The frequency converting module 21 transforms the tone signals yml(t) and ymr(t), and the audio signal 5*b* (x(t)) into the tone signals (spectrum) on the frequency axis by cutting out the tone signals on the time axis with a given frame length and frame period, and performing frequency conversions by a windowing process, and then sends out the obtained spectra Yml(ω), Ymr(ω) and X(ω) to the impulse response calculating module 22. Further, the frequency converting module 21 sends out the obtained spectra Yml(ω) and Ymr(ω) also to the transfer function estimating module 24. Incidentally, the frequency converting module 21 executes a time-frequency conversion process, for example, Fast Fourier Transformation (FFT).

Here, X(ω)={X0(ω), X1(ω), . . . , XN−1(ω)}, where N is the number of frames, ω is a frequency. For example, X0(ω) is a spectrum of the tone signal at 0th frame.

Similarly, Yml(ω)={Yml0(ω), Yml1(ω), . . . , YmlN−1(ω)} and Ymr(ω)={Ymr0(ω), Ymr1(ω), . . . , YmrN−1(ω)}.

The impulse response calculating module (acquiring module) 22 calculates the impulse response Il(t) using the spectra Yml(ω) and X(ω) acquired from the frequency converting module 21 and calculates the impulse response Ir(t) using the spectra Ymr(ω) and X(ω) acquired from the frequency converting module 21. Specifically, the impulse response calculating module 22 calculates Yml(ω)/X(ω) and Ymr(ω)/X(ω), and thereafter, transforms with an inverse frequency conversion process (e.g., inverse Fourier transformation) into the tone signals Il(t) and Ir(t) on the time axis, which is set to be the impulse response (transfer function), for example.

Therefore, the signal IFFT{Yml0(ω)/X0(ω)} on the time axis transformed from Yml0(ω)/X0(ω) with the inverse frequency conversion process is set to be the impulse response of the sounds between the sound source loud speaker 6*a* and the left side error microphone 8*a* at the 0th frame, for example. Similarly, the signal IFFT{Ymr0(ω)/X0(ω)} on the time axis transformed from Ymr0(ω)/X0(ω) with the inverse frequency conversion process is set to be the impulse response of the sounds between the sound source loud speaker 6*a* and the right side error microphone 9*a* at the 0th frame.

Incidentally, it may be that IFFT{aveYml(ω)/aveX(ω)} is calculated using spectra aveYml(ω) and aveX(ω) obtained by averaging the spectra Yml(ω) and X(ω) respectively in the time direction, and is set to be the impulse response between the sound source loud speaker 6*a* and the left side error microphone 8*a*. Similarly, it may be that IFFT{aveYmr(ω)/aveX(ω)} is calculated using spectra aveYmr(ω) and aveX(ω) obtained by averaging the spectra Ymr(ω) and X(ω) respectively in the time direction, and is set to be the impulse response between the sound source loud speaker 6*a* and the right side error microphone 9*a*.

Equation 1, Equation 2 or the like below can be used as a method for calculating the spectra aveYml(ω) aveYmr(ω) and aveX(ω) averaged in the time direction. Note that Equation 1 and Equation 2 are examples of calculating the spectra averaged with the 0th to (N−1)th frames.

The impulse response calculating module 22 sends out the calculated impulse responses Il(t) and Ir(t) to the impulse response comparing/selecting module 23.

$$\left.\begin{aligned} aveX(\omega) &= \frac{1}{N}\sum Xk(\omega) \quad && k = 0 \sim N-1 \\ aveYml(\omega) &= \frac{1}{N}\sum Ymlk(\omega) \quad && k = 0 \sim N-1 \\ aveYmr(\omega) &= \frac{1}{N}\sum Ymrk(\omega) \quad && k = 0 \sim N-1 \end{aligned}\right\} \quad \text{(Eq. 1)}$$

-continued $$\left.\begin{aligned} aveX(\omega, n) &= \alpha \times aveX(\omega, n-1) + (1-\alpha) \times Xn(\omega) \\ aveYml(\omega, n) &= \alpha \times aveYml(\omega, n-1) + (1-\alpha) \times Ymln(\omega) \\ aveYmr(\omega, n) &= \alpha \times aveYmr(\omega, n-1) + (1-\alpha) \times Ymrn(\omega) \\ &N\text{: number of frames} \\ &n = N-1 \\ &\alpha\text{: value close to 1 (for example, } \alpha = 0.99) \end{aligned}\right\} \quad \text{(Eq. 2)}$$

The impulse response comparing/selecting module 23 compares each of the impulse responses Il(t) and Ir(t) calculated by the impulse response calculating module 22 with the impulse response registered in the transform matrix table 5*a*. Then, the impulse response comparing/selecting module (specifying module) 23 selects the identification number corresponding to the impulse response closest to each of the calculated impulse responses Il(t) and Ir(t) from the transform matrix table 5*a* and notifies the transfer function estimating module 24 of the selected identification number.

Specifically, the impulse response comparing/selecting module 23 finds a cross-correlation value between the impulse response Il(t) calculated by the impulse response calculating module 22 and each of the impulse responses IlA(t), IlB(t), IlC(t), . . . registered in the transform matrix table 5*a*. The impulse response comparing/selecting module 23 then selects the identification number corresponding to one of the impulse responses IlA(t), IlB(t), IlC(t), . . . whose cross-correlation value calculated is the highest. Similarly, the impulse response comparing/selecting module 23 finds a cross-correlation value between the impulse response Ir(t) calculated by the impulse response calculating module 22 and each of the impulse responses IrA(t), IrB(t), IrC(t), . . . registered in the transform matrix table 5*a*. The impulse response comparing/selecting module 23 then selects the identification number corresponding to one of the impulse responses IrA(t), IrB(t), IrC(t), . . . whose cross-correlation value calculated is the highest.

If the identification numbers for the impulse responses Il(t) and Ir(t) notified by the impulse response comparing/selecting module 23 are the same, the transfer function estimating module (reading-out module) 24 reads out the transform matrix Ts corresponding to the notified identification number from the transform matrix table 5*a*. The transfer function estimating module (estimating module) 24 estimates spectra Ydl'(ω) and Ydr'(ω) at the positions of the ears of the listener using the read out transform matrix Ts and the spectra Yml(ω)) and Ymr(ω) acquired from the frequency converting module 21. Specifically, the transfer function estimating module 24 calculates the spectra Ydl'(ω) and Ydr'(ω) by multiplying each of the spectra Yml(ω) and Ymr(ω) by the transform matrix Ts.

The transfer function estimating module 24 calculates IFFT{aveYdl'(ω)/aveX(ω)} using the spectra aveYdl'(ω) and aveX(ω) obtained by averaging the estimated spectra Ydl'(ω) and X(ω) respectively in the time direction, and sets the IFFT{aveYdl'(ω)/aveX(ω)} to be the impulse response (transfer function) between the sound source loud speaker 6*a* and the left ears of the listener. Similarly, the transfer function estimating module 24 calculates IFFT{aveYdr'(ω)/aveX(ω)} using spectra aveYdr'(ω) and aveX(ω) obtained by averaging the estimated spectra Ydlr'(ω) and X(ω) respectively in the time direction, and sets the IFFT{aveYdr'(ω)/aveX(ω)} to be the impulse response (transfer function) between the sound source loud speaker 6*a* and the right ears of the listener.

Note that the impulse response comparing/selecting module 23 may select the identification number corresponding to the impulse response whose cross-correlation value is the highest among the cross-correlation values between the impulse response Il(t) and the each of the impulse responses IlA(t), IlB(t), IlC(t), . . . and the cross-correlation values between the impulse response Ir(t) and each of the impulse responses IrA(t), IrB(t), IrC(t), . . . In this case, the impulse response comparing/selecting module 23 notifies the transfer function estimating module 24 of the identification number corresponding to the highest impulse response, and the transfer function estimating module 24 then reads out the transform matrix Ts corresponding to the notified identification number from the transform matrix table 5*a*. Then, the transfer function estimating module 24 estimates spectra Ydl'(ω) and Ydr'(ω) at the positions of the ears of the listener using the read out transform matrix Ts and the spectra Yml(ω) and Ymr(ω) acquired from the frequency converting module 21, and further calculates the impulse responses IFFT{aveYdl'(ω)/aveX(ω)} and IFFT{aveYdr'(ω)/aveX(ω)} of the sounds between the sound source loud speaker 6*a* and each of the ears of the listener.

In addition, if the identification numbers for the impulse responses Il(t) and Ir(t) notified from the impulse response comparing/selecting module 23 are different from each other, the transfer function estimating module 24 generates the transform matrix of 2×2 by combining the transform matrix corresponding to the identification number for the impulse response Il(t) and the transform matrix corresponding to the identification number for the impulse response Ir(t). Specifically, the transfer function estimating module 24 generates Ts in Equation 3 below in case the transform matrix corresponding to the identification number for the impulse response Il(t) is TsA in Equation 3 below, and the transform matrix corresponding to the identification number for the impulse response Ir(t) is TsB in Equation 3 below.

$$\left.\begin{aligned} TsA &= \begin{bmatrix} a_A(\omega) & b_A(\omega) \\ c_A(\omega) & d_A(\omega) \end{bmatrix} \\ TsB &= \begin{bmatrix} a_B(\omega) & b_B(\omega) \\ c_B(\omega) & d_B(\omega) \end{bmatrix} \\ Ts &= \begin{bmatrix} a_A(\omega) & b_B(\omega) \\ c_A(\omega) & d_B(\omega) \end{bmatrix} \end{aligned}\right\} \quad \text{(Eq. 3)}$$

The transfer function estimating module 24 sends out the calculated impulse responses IFFT{aveYdl'(ω)/aveX(ω)} and IFFT{aveYdr'(ω)/aveX(ω)} between the sound source loud speaker 6*a* and the ears of the listener to the canceling sound generating module 25. The canceling sound generating module 25 generates a canceling sound to suppress the music on the basis of the audio signals outputted from the sound source loud speaker 6*a* at the positions of the ears of the listener on the basis of the impulse responses IFFT{aveYdl'(ω)/aveX(ω)} and IFFT{aveYdr'(ω)/aveX(ω)} acquired from the transfer function estimating module 24. The canceling sound generating module 25 sends out the generated the generated canceling sound signals to the canceling sound loud speaker 7*a* to output the canceling sounds via the canceling sound loud speaker 7*a*.

Note that, in some methods for generating the canceling sound signals by the canceling sound generating module 25, the transfer function estimating module 24 may not perform the inverse frequency conversion process but send out aveYdl'(ω)/aveX(ω) and aveYdr'(ω)/aveX(ω) to the canceling sound generating module 25. Further, the transfer function estimating module 24 may send out the spectral aveYdl'(ω) and aveYdr'(ω) at the positions of the ears of the listener to the canceling sound generating module 25.

With the process described above, the car audio system 1 according to Embodiment 1 can accurately estimate the transfer functions at the position of the ears of the listener on the basis of the transfer functions of the sound outputted from the sound source loud speaker 6*a* at the error microphones 8*a* and 9*a*, and the registered information of the transform matrix table 5*a*.

Hereinafter, description will be given of a noise suppressing process in the car audio system 1 according to Embodiment 1 on the basis of an operation chart. Incidentally, the following process is executed by the arithmetic processing module 2 according to the control program stored in the ROM 3 or the storage module 5 of the car audio system 1.

Figure 5:
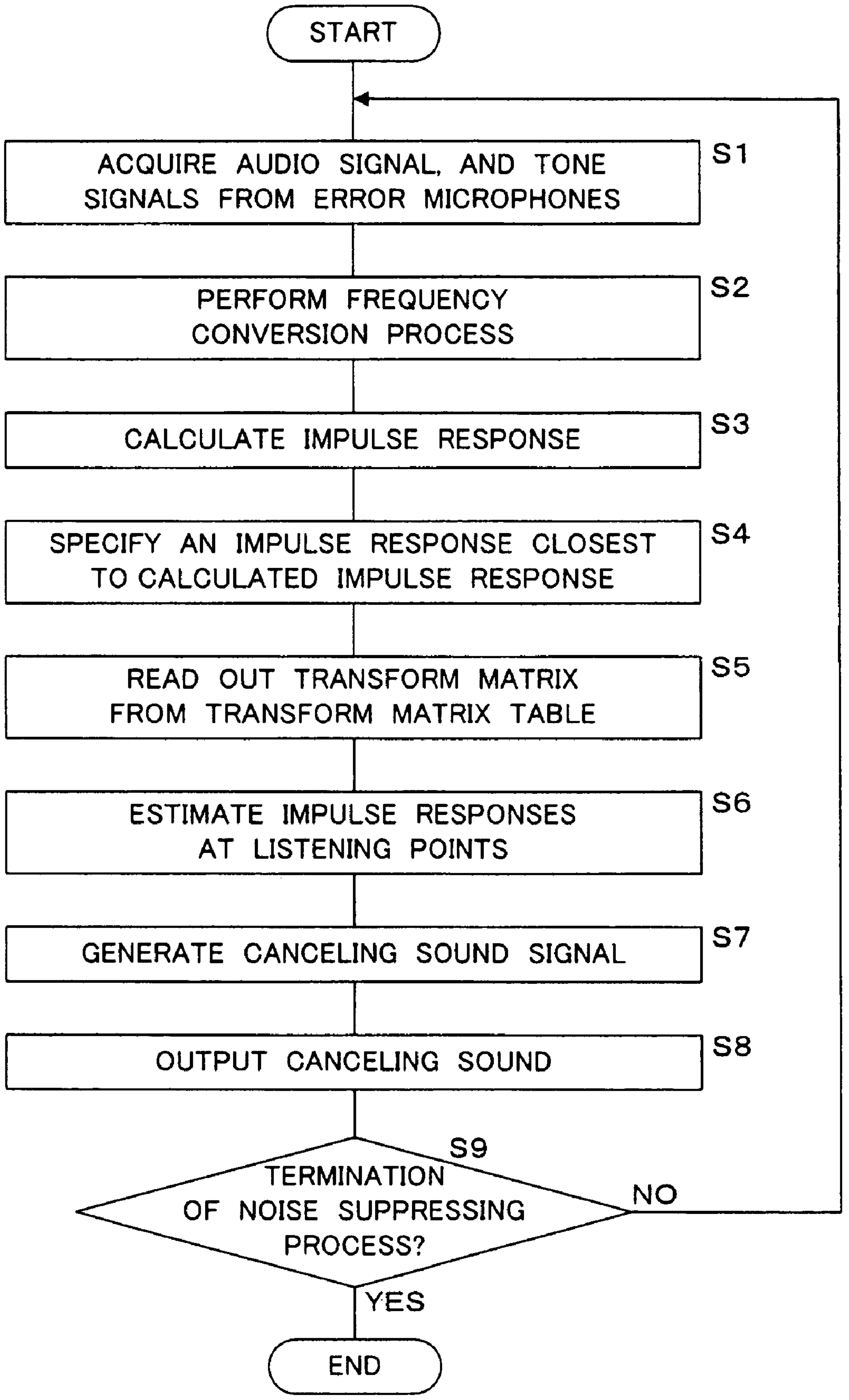
FIG. 5 is an operation chart illustrating an example of a procedure of a noise suppressing process.

Referring to FIG. 5, the arithmetic processing module 2 of the car audio system 1 acquires the audio signal 5*b* (x(t)), and the tone signals yml(t) and ymr(t) from the error microphones 8*a* and 9*a* (sound input modules 8 and 9), respectively, in a case which outputting the audio signal 5*b* from the sound source loud speaker 6*a* is started, for example (at S1). The arithmetic processing module 2 (frequency converting module 21) performs the frequency conversion process for the audio signal 5*b* (x(t)) and the tone signals yml(t) and ymr(t) acquired (at S2) to acquire the spectra X(ω), Yml(ω) and Ymr(ω).

The arithmetic processing module 2 (impulse response calculating module 22) calculates the impulse response Il(t) using the spectra Yml(ω) and X(ω) and calculates the impulse response Ir(t) using the spectra Ymr(ω) and X(ω) (at S3). The arithmetic processing module 2 (impulse response comparing/selecting module 23) specifies the impulse response closest to each of the calculated impulse responses Il(t) and Ir(t) among the impulse responses registered in the transform matrix table 5*a* (at S4), and selects the identification number corresponding to the specified impulse response from the transform matrix table 5*a*.

The arithmetic processing module 2 (transfer function estimating module 24) reads out from the transform matrix table 5*a* the transform matrix Ts corresponding to the identification number selected from the transform matrix table 5*a* (at S5), and estimates the impulse responses IFFT{aveYdl'(ω)/aveX(ω)} and IFFT{aveYdr'(ω)/aveX(ω)} at the listening points (positions of the ears of the listener) using the read out transform matrix Ts and the spectra Yml(ω), Ymr(ω) and X(ω) obtained in operation S2 (at S6).

The arithmetic processing module 2 (canceling sound generating module 25) generates such a canceling sound signal that suppresses the music outputted from the sound source loud speaker 6*a* at the positions of the ears of the listener on the basis of the estimated impulse responses at the estimated listening points (at S7). The arithmetic processing module 2 outputs the canceling sound on the basis of the generated canceling sound signal via the canceling sound loud speaker 7*a* (at S8).

The arithmetic processing module 2 determines whether or not a termination of the noise suppressing process of the car audio system 1 is instructed (at S9). For example, if outputting of the audio signal 5*b* from the sound source loud speaker 6*a* is terminated, or if the user instructs the termination of the noise suppressing process, the arithmetic processing module 2 determines the termination of the noise suppressing process is instructed. The arithmetic processing module 2, if determining the termination of the noise suppressing process is not instructed (at S9: NO), returns the process to operation S1 to repeat the processes of steps S1 to S8. The arithmetic processing module 2, if determining the termination of the noise suppressing process is instructed (at S9: YES), terminates the noise suppressing process described above.

Figure 6:
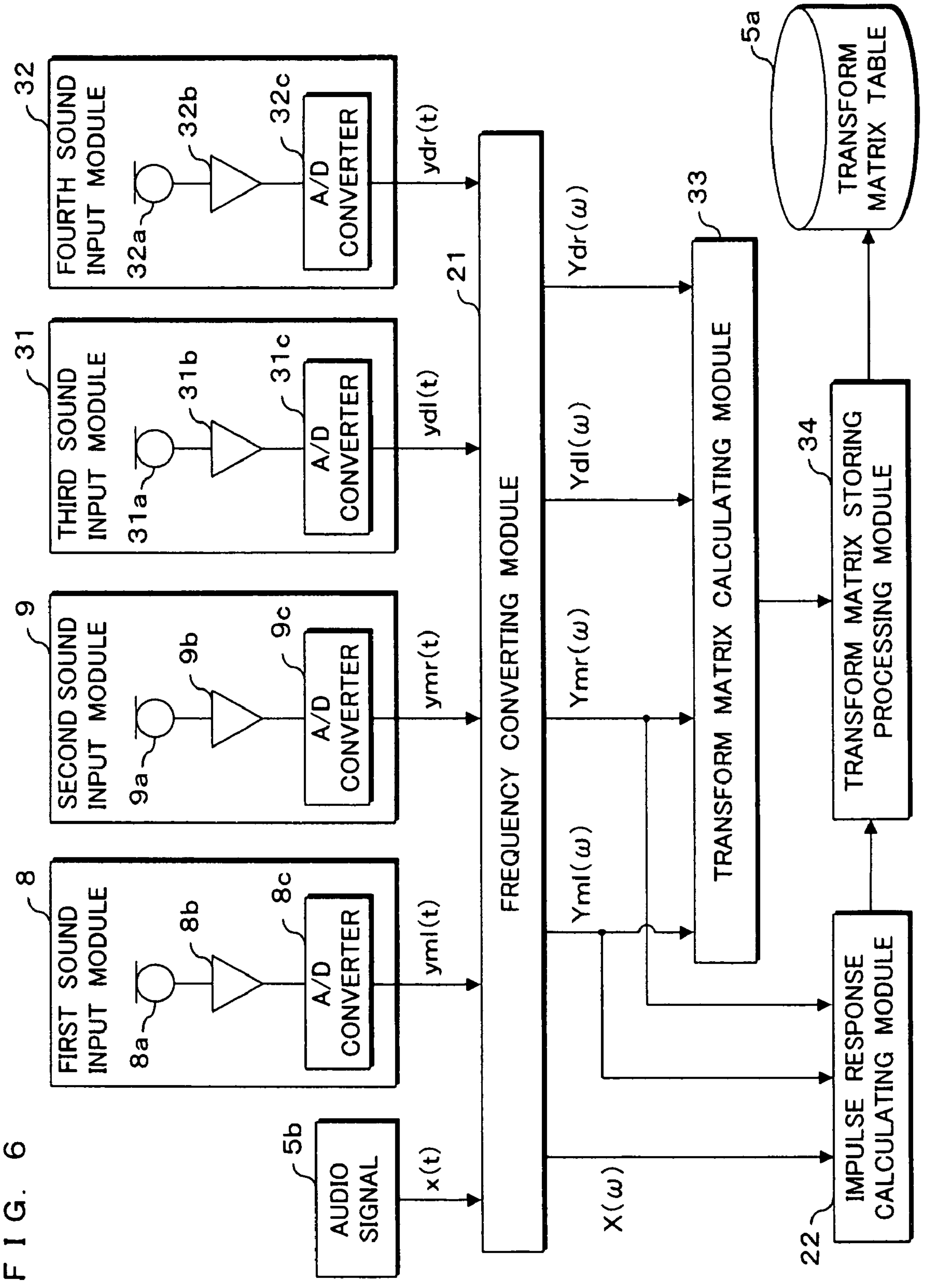
FIG. 6 is a functional block diagram illustrating an example of a functional configuration of the car audio system according to Embodiment 1.

Hereinafter, description will be given of the generating process of the transform matrix table 5*a* of the car audio system 1 including the above described configurations conducted before shipment from the factory. Referring to FIG. 6, in the car audio system 1 according to Embodiment 1, the arithmetic processing module 2 implements each of functions of a transform matrix calculating module 33, a transform matrix storing processing module 34 and the like in addition to the frequency converting module 21 and the impulse response calculating module 22 illustrated in FIG. 4, by executing the control program stored in the ROM 3 when conducting the generating process of the transform matrix table 5*a*.

Further, in the car audio system 1 according to Embodiment 1, when conducting the generating process of the transform matrix table 5*a*, a dummy head is installed in place of the listener (driver) and listening point microphones 31*a* and 32*a* are attached to the ears of the dummy head, in addition to the configuration illustrated in FIG. 1. Incidentally, the listening point microphones 31*a* and 32*a* are coupled with the body of the car audio system 1 via a cable, for example.

A third sound input module (a tone signal acquiring module) 31 has a left side listening point microphone 31*a*, an amplifier 31*b* and an A/D converter 31*c*. A fourth sound input module (a tone signal acquiring module) 32 has a right listening point microphone 32*a*, an amplifier 32*b* and an A/D converter 32*c*. Incidentally, the left side listening point microphone 31*a* is attached to the left ears of the dummy head arranged at the position of the listener illustrated in FIG. 1, and the right side listening point microphone 32*a* is attached to the right ears of the dummy head arranged at the position of the listener as illustrated in FIG. 1.

The listening point microphones 31*a* and 32*a* are capacitor microphones, for example, and generate the analog tone signals on the basis of the received sounds and send out the generated tone signals to the amplifiers 31*b* and 32*b*, respectively. The amplifiers 31*b* and 32*b* are gain amplifiers, for example, and amplify the tone signals inputted from the microphones 31*a* and 32*a* and send out the resultant tone signals to the A/D converters 31*c* and 32*c*, respectively. The A/D converters 31*c* and 32*c* convert the tone signals inputted from the amplifiers 31*b* and 32*b* into digital tone signals by sampling with a given sampling frequency using a filter such an LPF. The third sound input module 31 and the fourth sound input module 32 sends out the digital tone signals obtained by the A/D converters 31*c* and 32*c* to given output destinations, respectively.

A third sound input module 31 and a fourth sound input module 32 respectively sends out the tone signals ydl(t) and ydr(t) obtained by receiving the sounds to the frequency converting module 21. Note that "t" is the number of samples.

In a case of conducting the generating process of the transform matrix table 5*a*, the frequency converting module 21 is input with the audio signal 5*b* and the tone signals from the sound input modules 8, 9, 31 and 32. The frequency converting module 21 transforms the tone signals on the time axis into the tone signals (spectra) Yml(ω), Ymr(ω), Ydl(ω), Ydr(ω) and X(ω) on the frequency axis with respect to the tone signals yml(t), ymr(t), ydl(t) and ydr(t) as well as the audio signal 5*b* (x(t)).

The frequency converting module 21 sends out the obtained spectra Yml(ω), Ymr(ω), Ydl(ω) and Ydr(ω) to the transform matrix calculating module 33, and sends out the obtained spectra Yml(ω), Ymr(ω) and X(ω) to the impulse response calculating module 22.

The impulse response calculating module (transfer function acquiring module) 22 calculates the impulse response (transfer function) Il(t) using the spectra Yml(ω) and X(ω) acquired from the frequency converting module 21, and calculates the impulse response (transfer function) Ir(t) using the spectra Ymr(ω) and X(ω) acquired from the frequency converting module 21. Note that the impulse responses are, for example, Il(t)=IFFT{aveYml(ω)/aveX(ω)} and Ir(t)=IFFT{aveYmr(ω)/aveX(ω)}. The impulse response calculating module 22 sends out the calculated impulse responses Il(t) and Ir(t) to the transform matrix storing processing module 34.

The transform matrix calculating module (transformation coefficient acquiring module) 33 generates the transform matrix for transforming the spectra Yml(ω) and Ymr(ω) into the spectra Ydl(ω) and Ydr(ω) on the basis of the spectra Yml(ω), Ymr(ω), Ydl(ω) and Ydr(ω) acquired from the frequency converting module 21. Specifically, assuming that the transform matrix Ts of 2×2 is Equation 4 below, Ts is found by calculating Equation 5 below for every frequency.

$$Ts = \begin{bmatrix} a(\omega) & b(\omega) \\ c(\omega) & d(\omega) \end{bmatrix} \quad \text{(Eq. 4)}$$

$$\begin{bmatrix} a(\omega) & b(\omega) \\ c(\omega) & d(\omega) \end{bmatrix} \begin{bmatrix} Yml(\omega) \\ Ymr(\omega) \end{bmatrix} = \begin{bmatrix} Ydl(\omega) \\ Ydr(\omega) \end{bmatrix} \quad \text{(Eq. 5)}$$

Incidentally, in case of calculating the transform matrix Ts for a frequency f, X(f)={X0(f), X1(f), . . . , XN−1(f)}, Yml(f)={Yml0(f), Yml1(f), . . . , YmlN−1(f)}, Ymr(f)={Ymr0(f), Ymr1(f), . . . , YmrN−1(f)}. However, among these, used is a frame only where all of the powers (signal values) of X(f), Yml(f) and Ymr(f) are equal to or more than a threshold set in advance when calculating the transform matrix Ts. This can reduce the influence of the noise. Additionally, the threshold of X(ω) is desirably set to be different from those of Yml(ω) and Ymr(ω).

The transform matrix calculating module 33 sends out the calculated transform matrix Ts to the transform matrix storing processing module 34. The transform matrix storing processing module 34 assigns the identification number to the impulse responses Il(t) and Ir(t) acquired from the impulse response calculating module 22 and to the transform matrix Ts acquired from the transform matrix calculating module 33, and stores the identification number, the impulse responses Il(t) and Ir(t), and the transform matrix Ts which are associated with one another in the transform matrix table 5*a*.

Figure 7A:
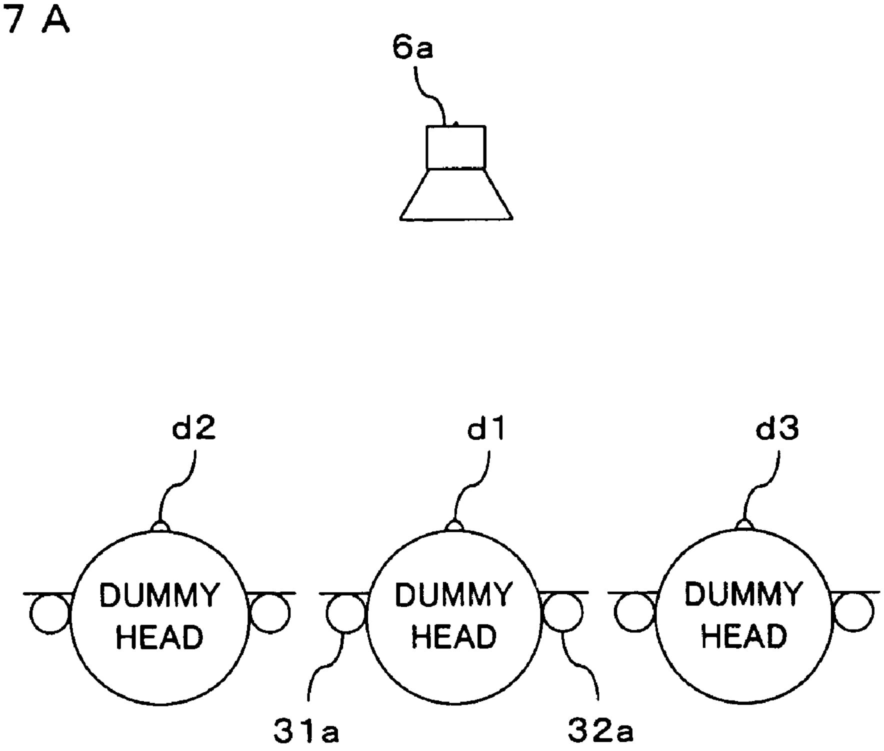
FIG. 7A and FIG. 7B are illustrations for explaining an example of a generating process of a transform matrix table.
Figure 7B:
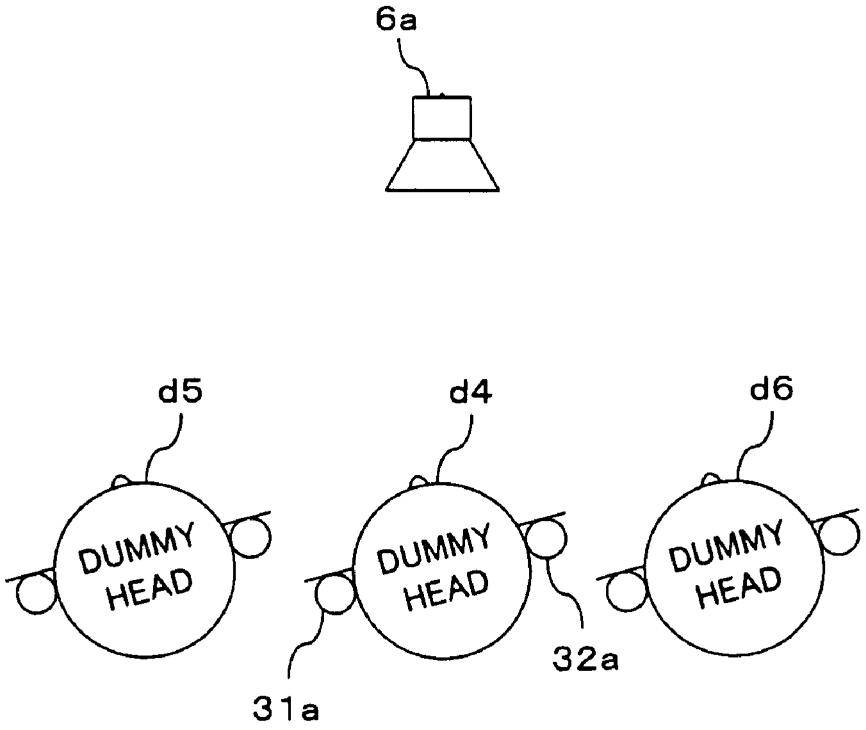

In the car audio system 1 of the above described configuration, when conducting the generating process of the transform matrix table 5*a*, a given audio signal 5*b* is outputted from the sound source loud speaker 6*a*, and the position of the dummy head is varied appropriately with respect to the sound source loud speaker 6*a* as illustrated in FIG. 7A and FIG. 7B. The reason why the position of the dummy head is varied appropriately and the transfer functions are registered in plural numbers in the transform matrix table 5*a* is so the position of the listening point is estimated from the sound transfer functions between the noise source 6*a* and the error microphones 8*a* and 9*a* using a phenomenon which changed is the sound transfer functions (impulse responses) between the noise source 6*a* and the error microphones 8*a* and 9*a* when the position of the listener and the position of the head of the listener are changed.

FIG. 7A depicts the dummy heads at positions d1, d2 and d3 shifted in a lateral direction with respect to the sound source loud speaker 6*a*. FIG. 7B depicts a state where the dummy heads at the positions d1, d2 and d3 illustrated in FIG. 7A are turned in an anticlockwise direction by a given angle. When the transform matrix table 5*a* is generated, the dummy head is shifted, for example, by a 5 cm interval with respect to the sound source loud speaker 6*a* in directions close to and apart from, in the left side direction and the right side direction, and in an upper direction and a lower direction.

Note that FIG. 7A and FIG. 7B depict respectively three positions of the dummy head to be shifted, but the positions are not limited to three in each shift direction, and desirably shifted appropriately in a range where the actual head position of the listener (driver) is possible to fall. Further, the dummy head is controlled to shift automatically by a 5 cm interval with respect to the sound source loud speaker 6*a* in directions close to and apart from, in the left side direction and the right side direction, and in an upper direction and a lower direction.

The arithmetic processing module 2 calculates the impulse responses Il(t) and Ir(t) and the transform matrix Ts for each position of the dummy head shifted to store in the transform matrix table 6*a* in series.

With the processes described above, the transform matrix table 5*a* can be generated where stored are the transfer functions at the position of the error microphone and the transform matrix for transforming the transfer functions into transfer functions at the position of each dummy head, which are associated with each other. With the noise suppressing process being conducted using the transform matrix table 5*a*, it is possible to more accurately estimate the transfer functions of the sound outputted from the sound source loud speaker 6*a* at the position of the ears of the listener. Therefore, it is possible to generate the canceling sound signal which suppresses the most effectively the sound outputted from the sound source loud speaker 6*a* at the position of the ears of the listener.

Hereinafter, description will be given of the generating process of the transform matrix table 5*a* in the car audio system 1 according to Embodiment 1 on the basis of an operation chart. Note that the following process is executed by the arithmetic processing module 2 according to the control program stored in the ROM 3 or the storage module 5 of the car audio system 1.

Figure 8:
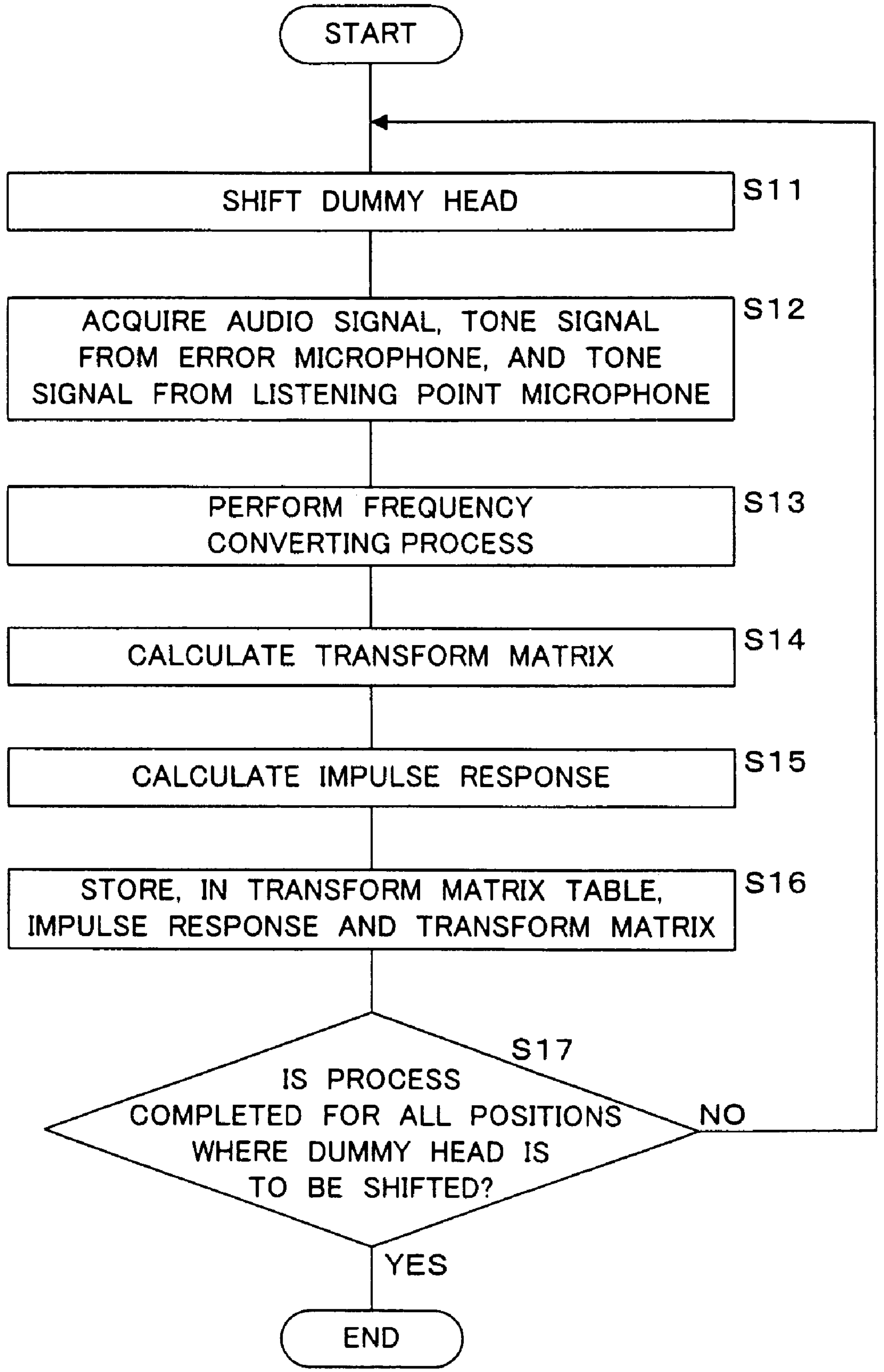
FIG. 8 is an operation chart illustrating an example of a procedure of the generating process of the transform matrix table.

Referring to FIG. 8, the arithmetic processing module 2 of the car audio system 1 shifts the dummy head to a given position when execution of the generating process of the transform matrix table 5*a* is instructed (at S11). The arithmetic processing module 2 acquires the audio signal 5*b* (x(t)), the tone signals yml(t) and ymr(t) from the error microphones 8*a* and 9*a* (sound input modules 8 and 9), and the tone signals ydl(t) and ydr(t) from the listening point microphones 31*a* and 32*a* (sound input modules 31 and 32) (at S12). The arithmetic processing module 2 conducts the frequency conversion process for the acquired audio signal 5*b* (x(t)), and tone signals yml(t), ymr(t), ydl(t) and ydr(t) (at S13) to acquire the spectra X(ω),Yml(ω), Ymr(ω), Ydl(ω) and Ydr (ω).

The arithmetic processing module 2 calculates the transform matrix Ts for transforming the spectra Yml(ω) and Ymr (c) into the spectra Ydl(ω) and Ydr(ω) on the basis of the acquired spectra Yml(ω), Ymr(ω), Ydl(ω) and Ydr(ω) (at S14). Incidentally, at this time, the arithmetic processing module 2 uses a frame only where each of the powers of X(f), Yml(f) and Ymr(f) for a frequency are equal to or more than a threshold set in advance to calculate the transform matrix Ts.

The arithmetic processing module 2 calculates the impulse response Il(t) using the spectra Yml(ω) and X(ω) acquired in operation S13, and calculates the impulse response Ir(t) using the spectra Ymr(ω) and X(ω) (at S15). The arithmetic processing module 2 associates the impulse responses Il(t) and Ir(t) calculated in operation S15 with the transform matrix Ts calculated in operation S14 to store in the transform matrix table 5*a* (at S16).

The arithmetic processing module 2 determines whether or not the process is completed for all positions where the dummy head is to be shifted (at S17). If determined the process is not completed (at S17: NO), the arithmetic processing module 2 returns the process to operation S11 to repeat the processes of steps S11 to S16. The arithmetic processing module 2, if determining the process is completed for all positions (at S17: YES), terminates the generating process of the transform matrix table 5*a* described above.

With the configuration described above, the car audio system 1 according to Embodiment 1 estimates the transfer functions at the listening point on the basis of the transfer functions of the sounds received by the error microphones 8*a* and 9*a* each of which is provided a position different from that of the listening point (ears of the listener). Therefore, if the listening point is moved, the transfer functions at the listening point can be accurately estimated.

There is an experimental result where in a case of establishing an active noise controller using the audio signals as the noise source, if the positions of the ears of the listener are apart from the error microphones 8*a* and 9*a*, a suppressed amount of noise is reduced by approximately 5 dB compared with the position of the error microphones 8*a* and 9*a*. However, if the transfer function estimating device applied to the car audio system 1 according to Embodiment 1 is used to generate the canceling sound signals using the transfer functions estimated by this transfer function estimating device, the suppressed amount of noise equivalent to the case where the error microphones 8*a* and 9*a* are installed at the positions of the ears of the listener can be obtained.

The car audio system 1 according to Embodiment 1 described above has a configuration of two error microphones 8*a* and 9*a* being provided, but the number of error microphones is not limited to two. Additionally, the number of the loud speakers 6*a* and 7*a* is not limited to two. Further, in Embodiment 1 described above, the description is given of the configuration as an example where the music on the basis of the audio signals is outputted from the sound source loud speaker 6*a* and the canceling sound is outputted from the canceling sound loud speaker 7*a*. However, the individual speakers 6*a* and 7*a* may be switched for reproducing music and for outputting the canceling sound to be used depending on the situation of the car audio system 1 being used. In addition, a configuration also may be such in which output are from the loud speaker 7*a* at the same time the music or the sound signal intended to be listened by the driver, and the canceling sound signal for suppressing the music outputted from the loud speaker 6*a*.

In the car audio system 1 according to Embodiment 1 described above, the configuration is in which the position of the dummy head with respect to the sound source loud speaker 6*a* is shifted when generating the transform matrix table 5*a*. In addition to such a configuration, the head size of the dummy head (distance between listening point microphones 31*a* and 32*a*), the hairstyle of the dummy head and the like may be changed.

Embodiment 2

Hereinafter, a car audio system according to Embodiment 2 will be described. Incidentally, the car audio system according to Embodiment 2 can be implemented with a configuration including a similar configuration to the car audio system 1 according to Embodiment 1 described above. Therefore, the same reference numerals are attached in the similar configuration, and the description thereof will be omitted.

The car audio system 1 according to Embodiment 2 has a configuration where calculated is the transfer function (impulse response) of the sounds received by the error microphones 8*a* and 9*a* periodically (every one second, for example). The car audio system 1 according to Embodiment 2, when a degree of similarity between the impulse response calculated one second before and the present impulse response falls below a given threshold, estimates again the transfer functions at the listening point as it determines that the listening point (ears of the listener) is moved. Specifically, the car audio system 1 according to Embodiment 2 selects again the transform matrix from the transform matrix table 5*a*.

As for an index used for the calculation of the degree of similarity between the impulse response calculated one second before and the present impulse response, there can be used, the cross-correlation value of the impulse responses, a spectral distance of the impulse responses and a cepstral distance of the impulse responses, for example.

In a case of using the cross-correlation value of the impulse responses, the arithmetic processing module 2 calculates cross-correlation values Cr(Il1(t), Il0(t)), Cr(Ir1(t), Ir0(t)) between the impulse responses Il1(t) and Ir1(t) of the sound received one second before by the error microphones 8*a* and 9*a* and the impulse responses Il0(t) and Ir0(t) presently received by the error microphones 8*a* and 9*a*. The arithmetic processing module 2, when at least one of the calculated cross-correlation values Cr(Il1(t), Il0(t)), Cr(Ir1(t), Ir0(t)) falls below a given threshold, selects again the transform matrix from the transform matrix table 5*a*. Note that a configuration may be in which the arithmetic processing module 2, when a value {Cr(Il1(t), Il0(t))}+{Cr(Ir1(t), Ir0(t))} obtained by adding the calculated cross-correlation values Cr(Il1(t), Il0(t)), Cr(Ir1(t), Ir0(t)) to each other falls below a given threshold, selects again the transform matrix from the transform matrix table 5*a*.

Additionally, in a case of using the spectral distance of the impulse responses, the arithmetic processing module 2 conducts the frequency conversion process for the impulse responses Il(t) and Ir(t) of the sounds received by the error microphones 8*a* and 9*a* to acquire the spectra. Then, the arithmetic processing module 2 calculates spectral distances D(Sl1(ω), Sl0(ω)), D(Sr1(ω), Sr0(ω)) between spectra Sl1(ω) and Sr1(ω) of the impulse responses Il1(t) and Ir1(t) of the sounds received one second before by the error microphones 8*a* and 9*a* and spectra Sl0(ω) and Sr0(ω) of the impulse responses Il0(t) and Ir0(t) of the sounds received presently by the error microphones 8*a* and 9*a*.

The arithmetic processing module 2, when at least one of the calculated spectral distances D(Sl1(ω), Sl0(ω)), D(Sr1(ω), Sr0(ω)) is equal to or more a given threshold, selects again the transform matrix from the transform matrix table 5*a*. Note that a configuration may be in which the arithmetic processing module 2, when a value {D(Sl1(ω), Sl0(ω))}+{D(Sr1(ω), Sr0(ω)} obtained by adding the calculated spectral distances D(Sl1(ω), Sl0(ω)), D(Sr1(ω), Sr0(ω)) to each other is equal to or more a given threshold, selects again the transform matrix from the transform matrix table 5*a*. Equation 6 below and the like can be used as a method for calculating the spectral distance. Further, the smaller the value of the spectra distance, the higher the degree of similarity of both impulse responses.

$$\left.\begin{aligned} D(Sl1(\omega),\ Sl0(\omega)) &= \sqrt{\sum_{\omega=1}^{n} (|Sl1(\omega)| - |Sl0(\omega)|)^2} \\ D(Sr1(\omega),\ Sr0(\omega)) &= \sqrt{\sum_{\omega=1}^{n} (|Sr1(\omega)| - |Sr0(\omega)|)^2} \end{aligned}\right\} \quad \text{(Eq. 6)}$$

$n$: point corresponding to Nyquist frequency $Sl0(\omega)$: spectrum of impulse response $Il0(t)$ $Sl1(\omega)$: spectrum of impulse response $Il1(t)$ $Sr0(\omega)$: spectrum of impulse response $Ir0(t)$ $Sr1(\omega)$: spectrum of impulse response $Ir1(t)$ Further, in a case of using the cepstral distance of the impulse responses, the arithmetic processing module 2 conducts the inverse frequency conversion process for a logarithm of an amplitude spectrum of the impulse responses Il(t) and Ir(t) of the sounds received by the error microphones 8*a* and 9*a* to acquire the cepstral distance. Then, the arithmetic processing module 2 calculates the cepstral distances Dcep (Cepl1(τ), Cepl0(τ)), Dcep(Cepr1(τ) and Cepr0(τ)) between cepstrums Cepl1(τ) and Cepr1(τ) of the impulse responses Il1(t) and Ir1(t) of the sounds received one second before by the error microphones 8*a* and 9*a* and cepstrums Cepl0(τ) and Cepr0(τ) of the impulse responses Il0(t) and Ir0(t) of the sounds received presently by the error microphones 8*a* and 9*a*.

The arithmetic processing module 2, when at least one of the calculated cepstral distances Dcep(Cepl1(τ), Cepl0(τ)), Dcep(Cepr1(τ) and Cepr0(τ)) is equal to or more a given threshold, selects again the transform matrix from the transform matrix table 5*a*. Note that a configuration may be in which the arithmetic processing module 2, when a value {Dcep(Cepl1(τ), Cepl0(τ)}+{Dcep(Cepr1(τ), Cepr0(τ)} obtained by adding cepstral distances Dcep(Cepl1(τ), Cepl0(τ)), Dcep(Cepr1(τ) and Cepr0(τ)) to each other is equal to or more a given threshold, selects again the transform matrix from the transform matrix table 5*a*. Equation 7 below and the like can be used as a method for calculating the cepstral distance. Further, the smaller the value of the cepstral distance, the higher the degree of similarity of both impulse responses. In a case of calculating the cepstrum distance using cepstrum up to pth power.

$$\left.\begin{aligned} D_{cep}(Cepl1(\tau),\ Cepl0(\tau)) &= \sqrt{\sum_{\tau=1}^{p} (Cepl1(\tau) - Cepl0(\tau))^2} \\ D_{cep}(Cepr1(\tau),\ Cepr0(\tau)) &= \sqrt{\sum_{\tau=1}^{p} (Cepr1(\tau) - Cepr0(\tau))^2} \end{aligned}\right\} \quad \text{(Eq. 7)}$$

$Cepl0(\tau)$: cepstrum of impulse response $Il0(t)$ $Cepl1(\tau)$: cepstrum of impulse response $Il1(t)$ $Cepr0(\tau)$: cepstrum of impulse response $Ir0(t)$ $Cepr1(\tau)$: cepstrum of impulse response $Ir1(t)$ Incidentally, in the calculating process described above, time averages aveIl1(t) and aveIr1(t) of the impulse responses until one second before may be used, instead of the impulse responses Il1(t) and Ir1(t) sounds received one second before by the error microphones 8*a* and 9*a*. Additionally, the time averages aveIl0(t) and aveIr0(t) of the impulse responses so far may be used, instead of the impulse responses Il0(t) and Ir0(t) of the sounds received presently by the error microphones 8*a* and 9*a*. Further, a time interval for calculating the impulse response (transfer function) is not limited to one second.

With the processes described above, the car audio system 1 according to Embodiment 2 estimates the transfer function at the position of the ears (listening point) of the listener on the basis of the transfer functions of the sound at the error microphones 8*a* and 9*a* outputted from the sound source loud speaker 6*a*. Further, the car audio system 1 estimates again the transfer function at the listening point when the transfer functions is changed at the error microphones 8*a* and 9*a*, while conducting the noise suppressing process using the estimated transfer function at the listening point. Therefore, if the sound transfer function is changed due to occurring change of a usage environment of the car audio system 1, the transfer function at the listening point is estimated again; thus, always enabling the noise suppressing process using the optimum transfer functions.

Hereinafter, description will be given of the noise suppressing process in the car audio system 1 according to Embodiment 2 on the basis of operation charts. Note that the following processes are executed by the arithmetic processing module 2 according to the control program stored in the ROM 3 or the storage module 5 of the car audio system 1.

Figure 9:
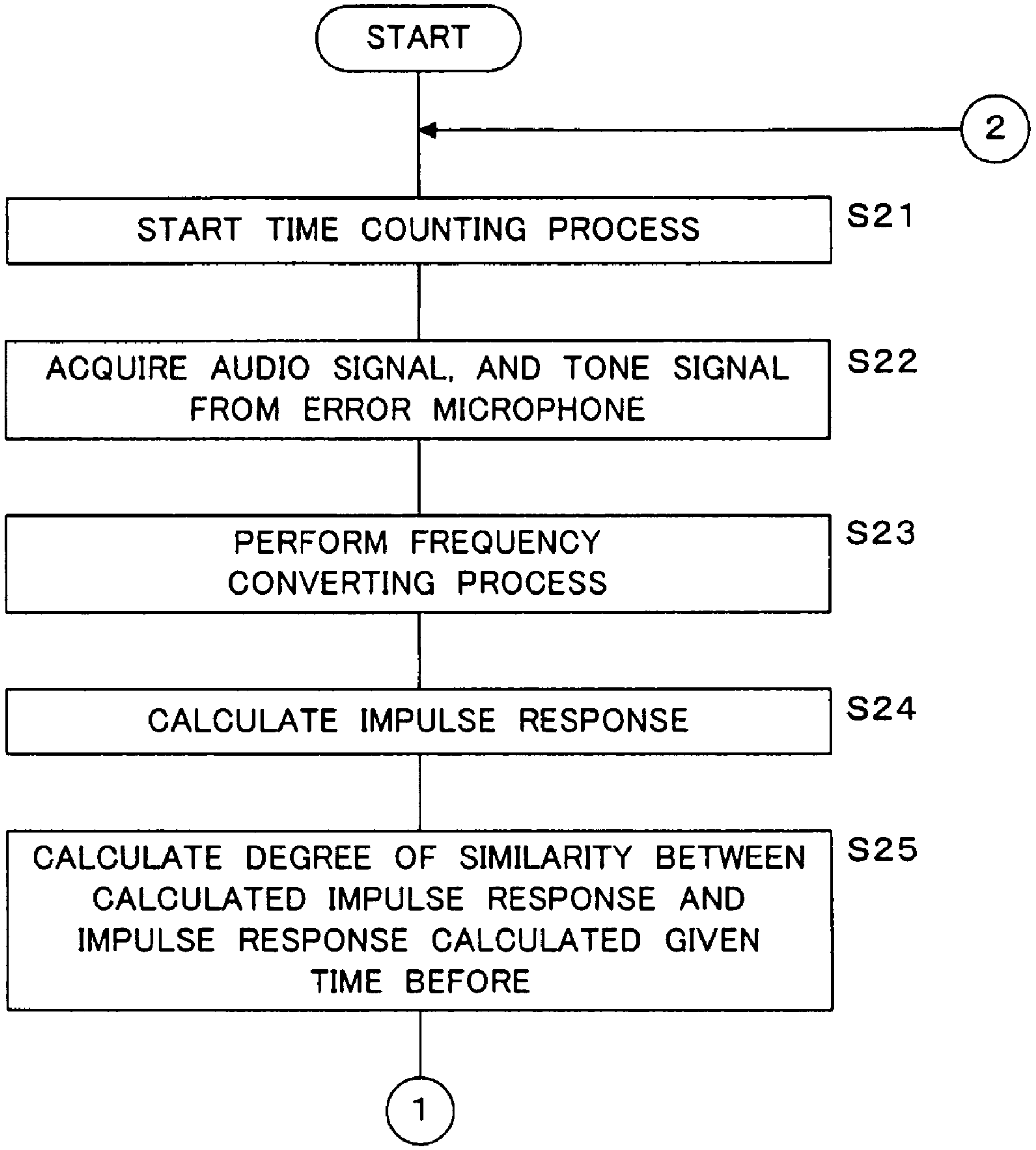
FIG. 9 is an operation chart illustrating an example of a procedure of a noise suppressing process of Embodiment 2.
Figure 10:
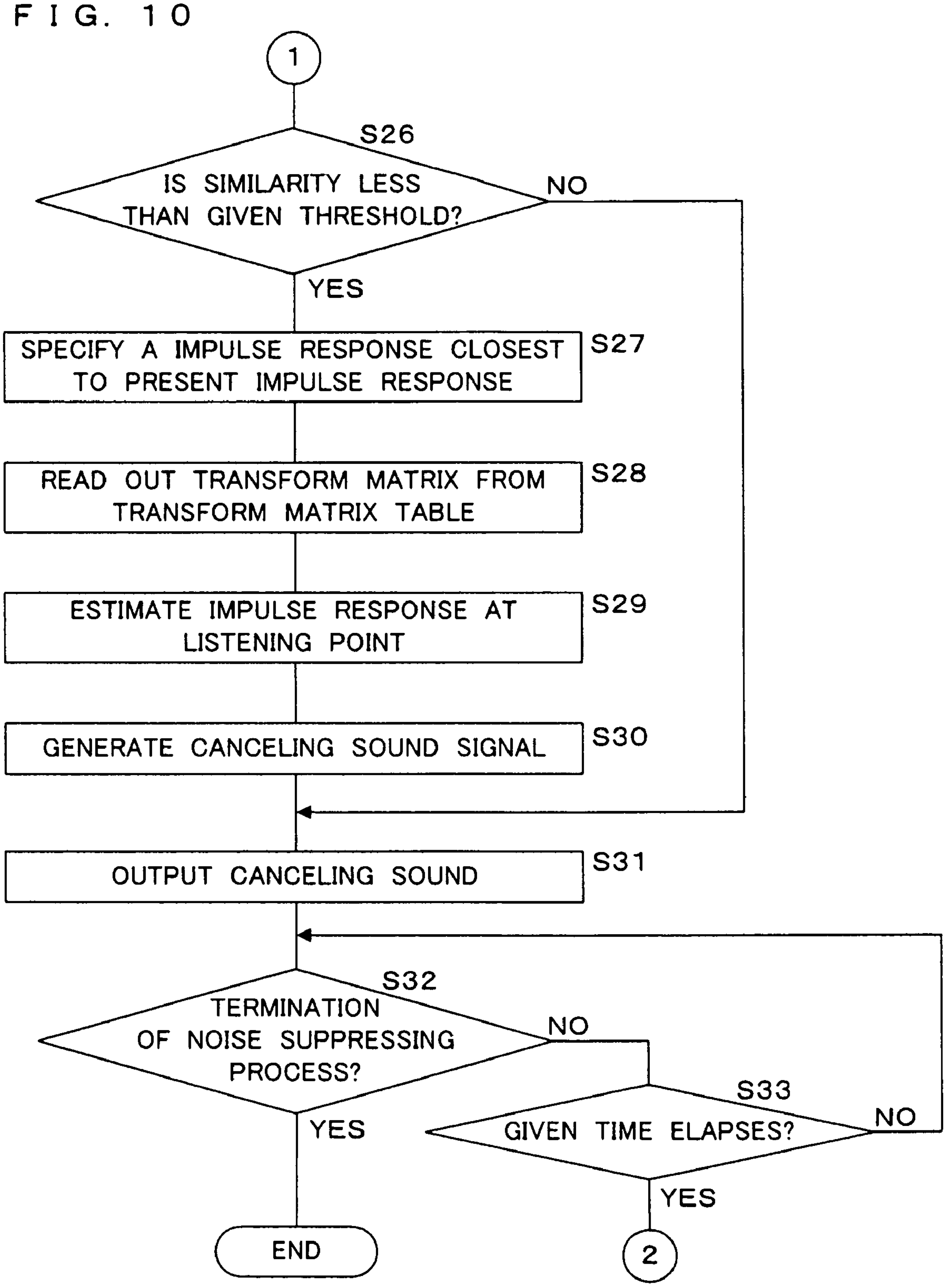
FIG. 10 is an operation chart illustrating an example of a procedure of the noise suppressing process of Embodiment 2.

Referring to FIG. 9 and FIG. 10, the arithmetic processing module 2 of the car audio system 1, for example, when outputting the audio signal 5*b* from the sound source loud speaker 6*a* is started, starts a time counting process with a clock (not illustrated) of itself (at S21). The arithmetic processing module 2 acquires the audio signal 5*b* (x(t)) and the tone signals yml(t) and ymr(t) from the error microphones 8*a* and 9*a* (sound input modules 8 and 9) (at S22). The arithmetic processing module 2 conducts the frequency conversion process for the audio signal 5*b* (x(t)), and the tone signals yml(t) and ymr(t) which are acquired (at S23) to obtain the spectra X(ω), Yml(ω) and Ymr(ω).

The arithmetic processing module 2 calculates the impulse response Il0(t) using the acquired spectra Yml(ω) and X(ω), and calculates the impulse response Ir0(t) using the acquired spectra Ymr(ω) and X(ω) (at S24). The arithmetic processing module 2 calculates the degree of similarities (e.g., the cross-correlation value) respectively between the calculated impulse responses Il0(t) and Ir0(t) and the impulse responses Il1(t) and Ir1(t) calculated a given time before (at S25).

Referring to FIG. 10, the arithmetic processing module 2 determines whether or not the calculated degree of similarity is less than a given threshold (at S26). Incidentally, the arithmetic processing module 2 has a configuration where the impulse responses Il1(t) and Ir1(t) calculated a previous time are stored in the RAM 4, but skips the processes of steps S25 and S26 if the impulse responses Il1(t) and Ir1(t) calculated a previous time are not stored in the RAM 4.

The arithmetic processing module 2, if determining the calculated degree of similarity is not less than a given threshold (at S26: NO), proceeds the process to operation S31. The arithmetic processing module 2, if determining the calculated degree of similarity is less than a given threshold (at S26: YES), specifies the impulse response closest to the present impulse responses Il0(t) and Ir0(t) calculated in step 24 among the impulse responses registered in the transform matrix table 5*a* (at S27) to select the identification number corresponding to the specified impulse response from the transform matrix table 5*a*.

The arithmetic processing module 2 reads out from the transform matrix table 5*a* the transform matrix Ts corresponding to the identification number selected from the transform matrix table 5*a* (at S28) to estimate the impulse responses IFFT{aveYdl'(ω)/aveX(ω)} and IFFT{aveYdr'(ω)/aveX(ω)} at the listening points (positions of the ears of the listener) using the read out transform matrix Ts and the spectra Yml(ω) and Ymr(ω) acquired in operation S23 (at S29).

The arithmetic processing module 2 generates the canceling sound signals to suppress the music outputted from the sound source loud speaker 6*a* at the ears position of the listener on the basis of the estimated impulse response at the listening point (at S30). The arithmetic processing module 2 outputs the canceling sound on the basis of the generated canceling sound signals via the canceling sound loud speaker 7*a* (at S31).

The arithmetic processing module 2 determines whether or not a termination of the noise suppressing process of the car audio system 1 is instructed (at S32). For example, if outputting of the audio signal 5*b* from the sound source loud speaker 6*a* is terminated, the arithmetic processing module 2 determines the termination of the noise suppressing process is instructed. The arithmetic processing module 2, if determining the termination of the noise suppressing process is not instructed (at S32: NO), determines whether or not a given time elapses on the basis of the time counting process started in step 21 (at S33).

The arithmetic processing module 2, if determining a given time does not elapse (at S33: NO), returns the process to operation S32 to wait until the process termination is instructed or the given time elapses. The arithmetic processing module 2, if determining the given time elapses (at S33: YES), returns the process to operation S21 to reset the time counting process, starts again the time counting process (at S21), and repeats the processes of steps S21 to S31. The arithmetic processing module 2, if determining the termination of the noise suppressing process is instructed (at S32: YES), terminates the noise suppressing process described above.

With the configuration described above, the car audio system 1 according to Embodiment 2 estimates again the transfer functions at the positions of the ears (listening points) of the listener when changes in the transfer functions of the sounds at the error microphones 8*a* and 9*a* occur, while conducting the noise suppressing process using the transfer functions at the estimated listening points. Therefore, it is possible to estimate the transfer function always at an optimum listening point to considerably suppress the sounds outputted from the sound source loud speaker 6*a* with the noise suppressing process using the transfer function like this.

Embodiment 3

Hereinafter, a car audio system according to Embodiment 3 will be described. Incidentally, the car audio system according to Embodiment 3 can be implemented with a configuration including a similar configuration to the car audio system 1 according to Embodiment 1 described above. Therefore, the same reference numerals are attached in the similar configuration, and the description thereof will be omitted.

The car audio system 1 according to Embodiment 1 described above has the configuration where a given audio signal 5*b* is outputted from the sound source loud speaker 6*a*, and the transform matrix table 5*a* is generated on the basis of the audio signal 5*b*, the tone signals of the sounds received by the error microphones 8*a* and 9*a*, and the tone signals of the sounds received by the listening point microphones 31*a* and 32*a*. The car audio system 1 according to Embodiment 3 has a configuration where the transform matrix table 5*a* is generated on the basis of not the audio signal 5*b*, but, for example a noise signal of noise such as engine sounds possible to generate in a vehicle, the tone signals of the sounds received by the error microphones 8*a* and 9*a*, and the tone signals of the sounds received by the listening point microphones 31*a* and 32*a*. That is, in Embodiment 3, the configuration is in which the car audio system 1 where the noise source is not a known signal generates the transform matrix table 5*a*.

Figure 11:
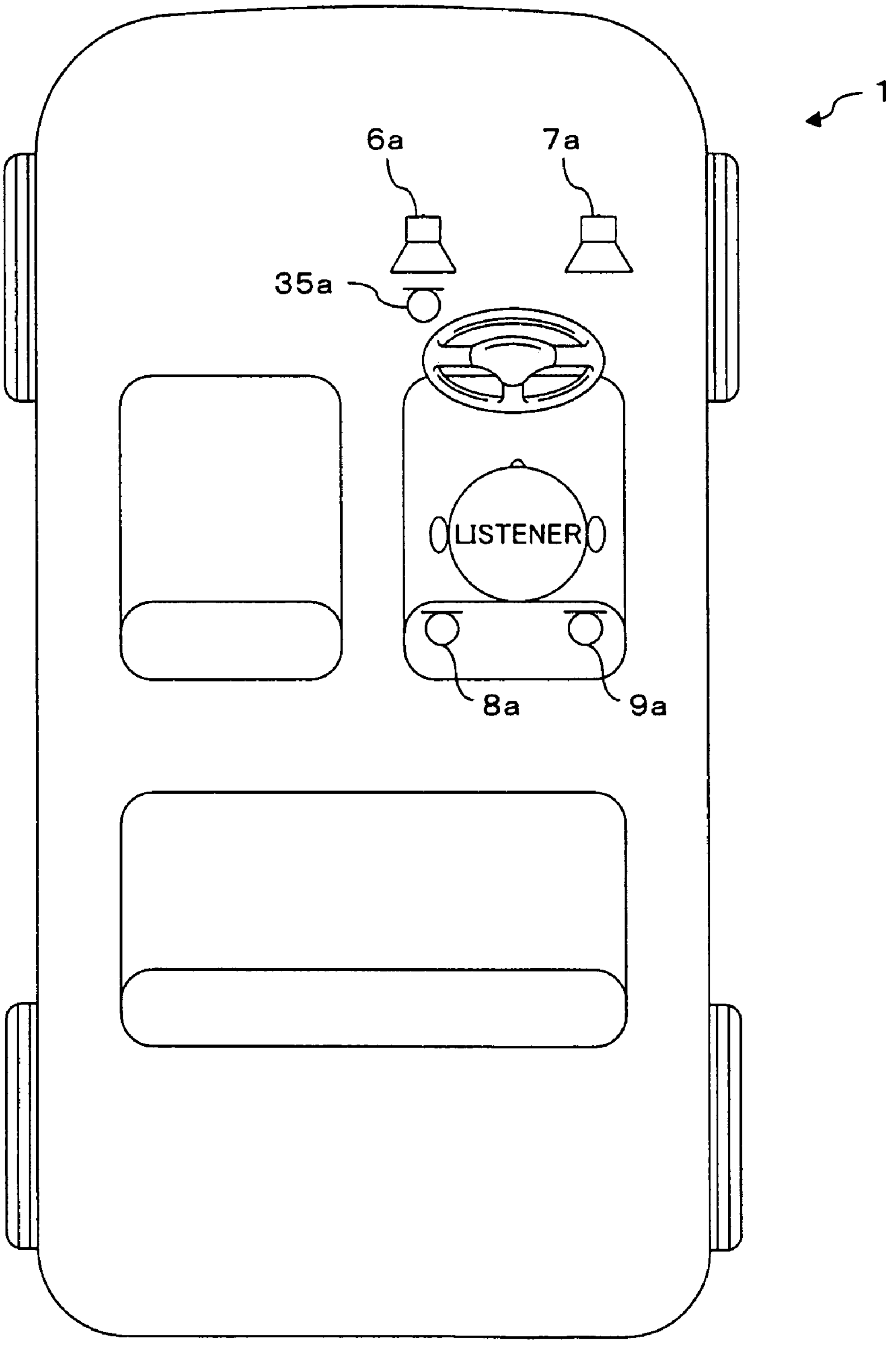
FIG. 11 is a schematic view illustrating an installation example of a car audio system according to Embodiment 3.

Referring to FIG. 11, in the car audio system according to Embodiment 3, when conducting the generating process of the transform matrix table 5*a*, a reference microphone 35*a* is installed in the vicinity of the sound source loud speaker 6*a*, in addition to the configuration illustrated in FIG. 1. Note that the reference speaker 35*a* is coupled to a body of the car audio system 1 via a cable, for example. FIG. 11 illustrates an example where the reference microphone 35*a* is provided in the vicinity of the sound source loud speaker 6*a*. However, the sound source loud speaker 6*a* is only assumed to be the noise source, and actually the reference microphone 35*a* is provided in the vicinity of the noise source.

Figure 12:
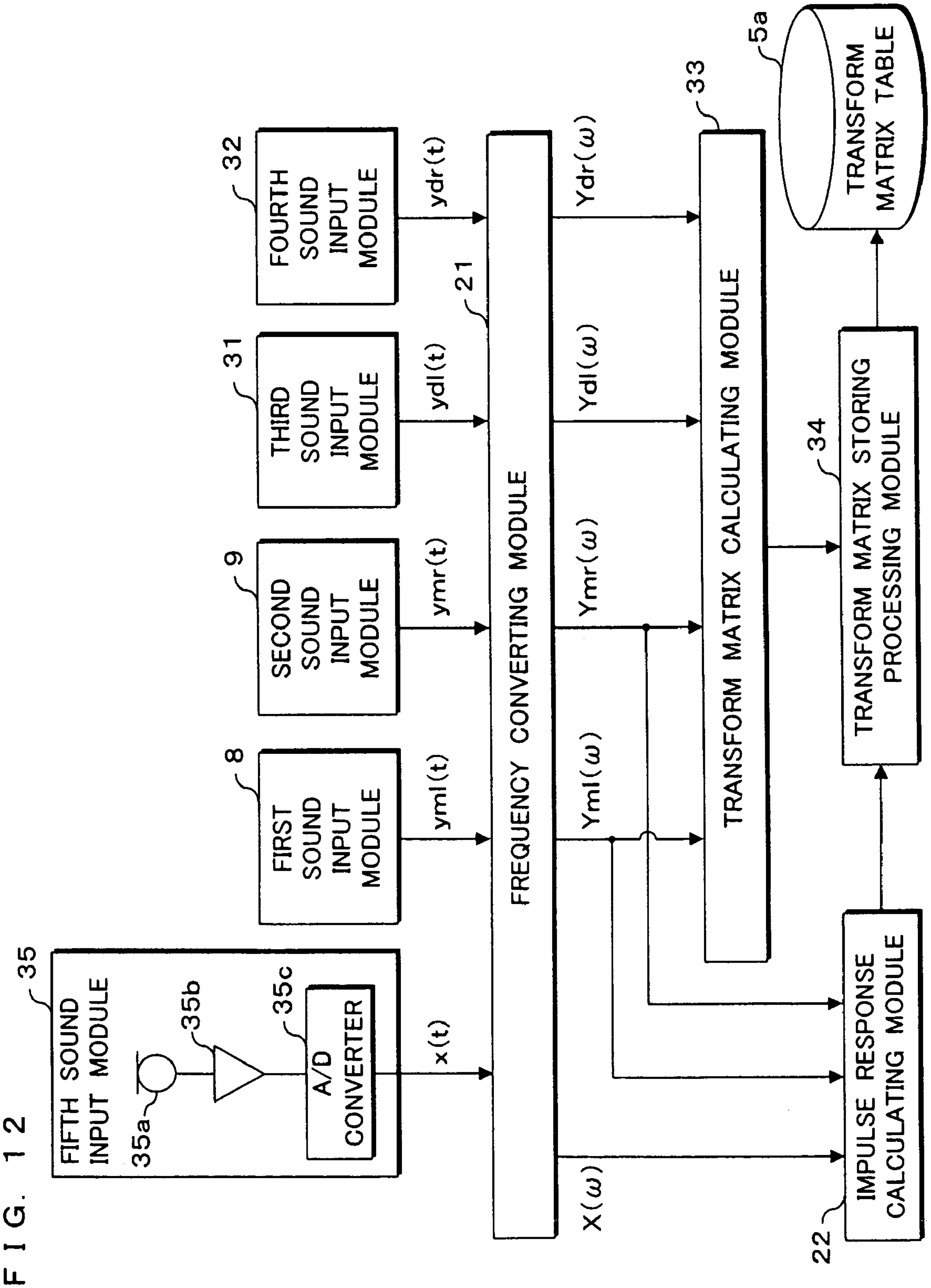
FIG. 12 is a functional block diagram illustrating an example of a functional configuration of the car audio system according to Embodiment 3.

Referring to FIG. 12, in the car audio system 1 according to Embodiment 3, a tone signal x(t) obtained by the reference microphone 35*a* receiving the sound is inputted to the frequency converting module 21, instead of the audio signal 5*b*.

A fifth sound input module 35 has the reference microphone 35*a*, an amplifier 35*b*, and an AID converter 35*c*. The reference microphone 35*a* is a capacitor microphone, for example, and generates the analog tone signal on the basis of the received sound and sends out the generated tone signal to the amplifier 35*b*.

The amplifier 35*b* is a gain amplifier, for example, and amplifies the tone signal inputted from the microphone 35*a* and sends out the resultant tone signal to the A/D converter 35*c*. The A/D converter 35*c* converts the tone signals inputted from the amplifier 35*b* into digital tone signals by sampling with a given sampling frequency using a filter such an LPF. The fifth sound input module 35 sends out the digital tone signal x(t) obtained by the A/D converter 35*c* to the frequency converting module 21.

The frequency converting module 21 of Embodiment 3, when conducting the generating process of the transform matrix table 5*a*, transforms the tone signals on the time axis into the tone signals (spectra) Yml(ω), Ymr(ω), Ydl(ω), Ydr(ω) and X(ω) on the frequency axis with respect to the tone signals yml(t), ymr(t), ydl(t) and ydr(t) from the sound input modules 8, 9, 31 and 32 as well as the tone signal x(t) inputted from the fifth input module 35.

Incidentally, the transform matrix calculating module 33, the transform matrix storing processing module 34, the impulse response calculating module 22 and the like perform similar processes to those described above in Embodiment 1; thus, the description thereof is omitted.

With the processes described above, even if the noise source intended to be suppressed in the car audio system 1 generates not only the audio signal 5*b* outputted from the sound source loud speaker 6*a* but also the noise generated in operating the vehicle, for example, the engine sound, the noise suppressing process can be well performed.

Embodiment 3 described above is explained as a modified example of Embodiment 1, but can also be applied to the configuration of Embodiment 2 described above.

Embodiment 4

Hereinafter, a car audio system according to Embodiment 4 will be described. Incidentally, the car audio system according to Embodiment 4 can be implemented with a similar configuration to the car audio system 1 according to Embodiment 1 described above. Therefore, the same reference numerals are attached in the similar configuration, and the description thereof will be omitted.

The car audio system 1 according to Embodiment 1 described above has the configuration where the identification number, the two transfer functions Il(t) and Ir(t), and the transformation coefficient Ts are registered in the transform matrix table 5*a* in a state of being associated with one another, in plural numbers. The car audio system 1 according to Embodiment 4 has a configuration where the identification number, information indicating positions of the ears of the dummy head, two transfer functions Il(t) and Ir(t), and the transformation coefficient Ts are registered in the transform matrix table 5*a* in a state of being associated with one another.

The car audio system 1 according to Embodiment 4 has a camera 12 installed at a position where an image of a face of the listener (driver) can be captured; the camera 12 being coupled to the body of the car audio system 1 via a cable, for example.

Figure 13:
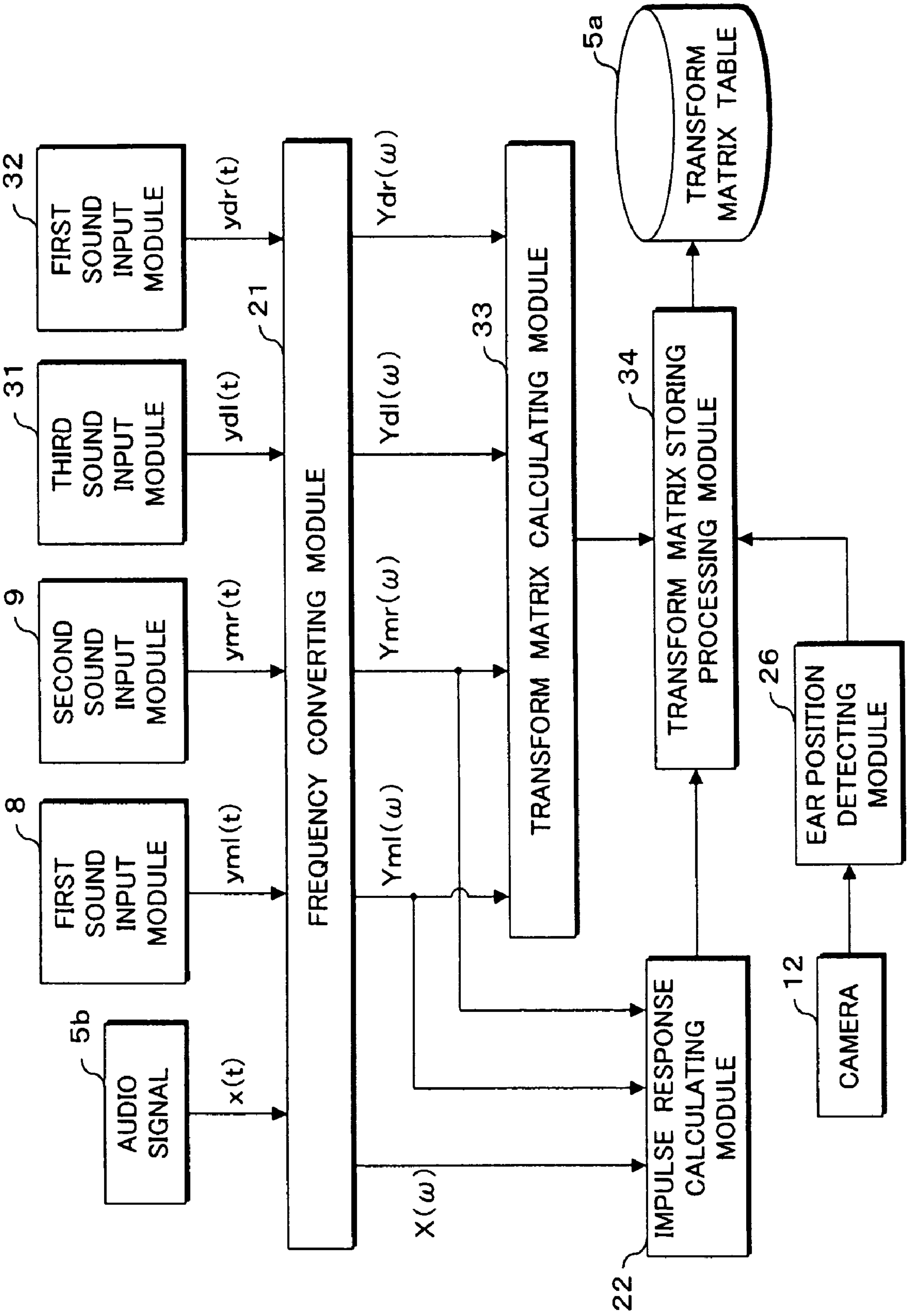
FIG. 13 is a functional block diagram illustrating an example of a functional configuration of a car audio system according to Embodiment 4.

Referring to FIG. 13, the arithmetic processing module 2 of Embodiment 4 has a function of an ears position detecting module 26 when conducting the generating process of the transform matrix table 5*a*, in addition to the configuration illustrated in FIG. 6. When the arithmetic processing module 2 conducts the generating process of the transform matrix table 5*a*, the camera 12 captures an image of a face of the dummy head arranged at the driver's seat, and the ears position detecting module (position detecting module) 26 detects the position of the ears of the dummy head (listening point) on the basis of the image data obtained by the camera 12. Incidentally, since the camera 12 is a fixed point camera, it may be the position of the detected ears is defined with a coordinate system including a reference point at a given point in an image-capturing range. The ears position detecting module 26 sends out the detected ears position information to the transform matrix storing processing module 34.

The transform matrix storing processing module 34 of Embodiment 4 attaches the identification number to the impulse responses Il(t) and Ir(t) acquired from the impulse response calculating module 22, the transform matrix Ts acquired from the transform matrix calculating module 33, and the ears position information acquired from the ears position detecting module 26, and associates the identification number, the impulse responses Il(t) and Ir(t), the transform matrix Ts, and the ears position information with one another to store in the transform matrix table 5*a*.

Hereinafter, the generating process of the transform matrix table 5*a* in the car audio system 1 according to Embodiment 4 is described on the basis of an operation chart. Incidentally, the following process is conducted by the arithmetic processing module 2 according to the control program stored in the ROM 3 or the storage module 5 of the car audio system 1.

Figure 14:
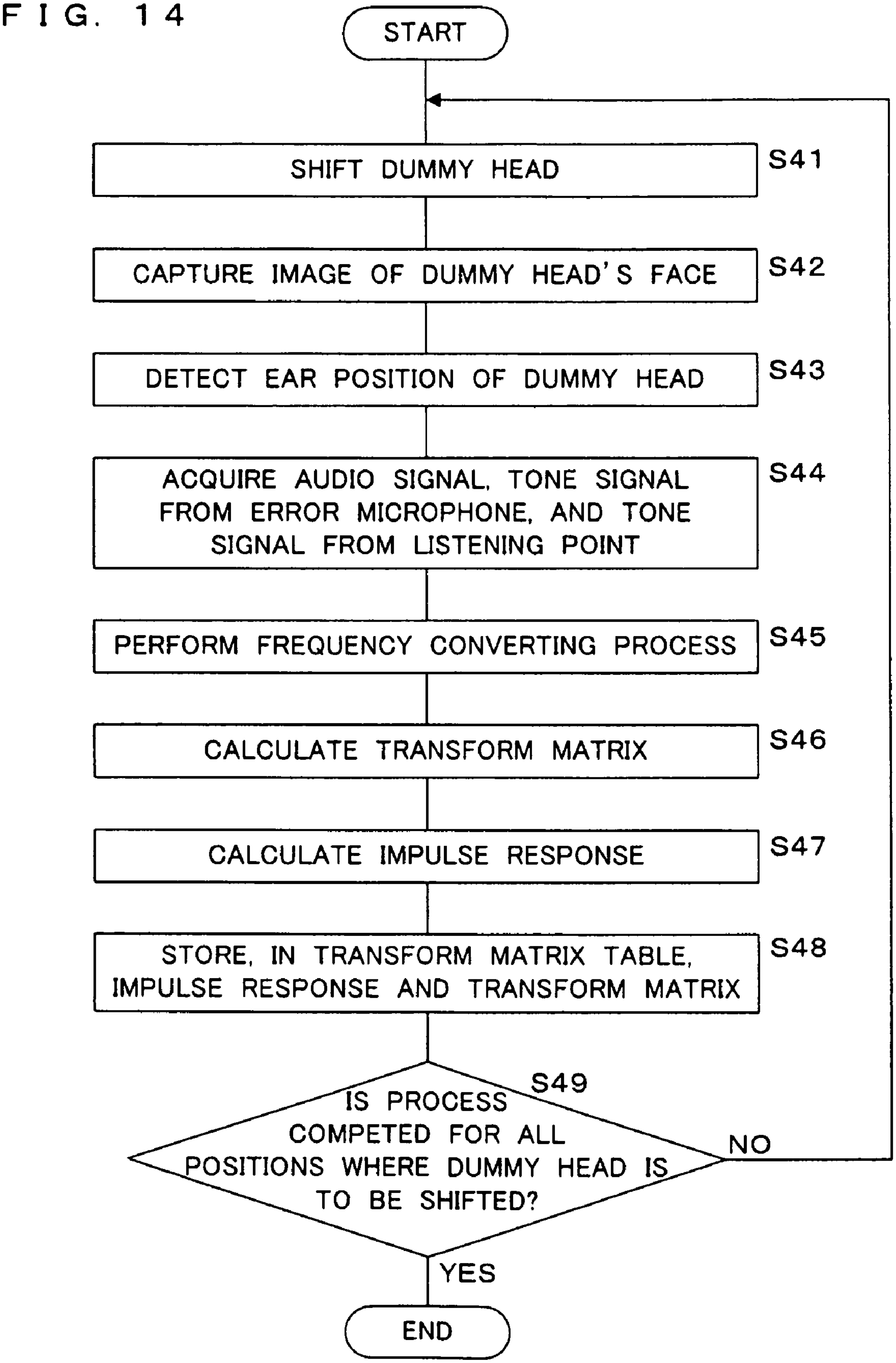
FIG. 14 is an operation chart illustrating an example of a procedure of a generating process of a transform matrix table.

Referring to FIG. 14, the arithmetic processing module 2 of the car audio system 1, when an execution of the generating process of the transform matrix table 5*a* is instructed, shifts the dummy head to a given position (at S41). The arithmetic processing module 2 captures an image of the dummy head's face with the camera 12 (at S42). The arithmetic processing module 2 (ears position detecting module 26) detects the ears position of the dummy head on the basis of the image data acquired from the camera 12 (at S43) to acquire the information representing the ears position.

The arithmetic processing module 2 acquires the audio signal 5*b* (x(t)), the tone signals yml(t) and ymr(t) from the error microphones 8*a* and 9*a*, and the tone signals ydl(t) and ydr(t) from the listening point microphones 31*a* and 32*a* (at S44). The arithmetic processing module 2 conducts the frequency conversion process for the audio signal 5*b* (x(t)), and tone signals yml(t), ymr(t), ydl(t) and ydr(t) which are acquired (at S45) to acquire the spectra X(ω), Yml(ω), Ymr (ω), Ydl(ω) and Ydr(ω). The arithmetic processing module 2 calculates the transform matrix Ts for transforming the spectra Yml(ω) and Ymr(ω) into the spectra Ydl(ω) and Ydr((ω) on the basis of the obtained spectra Yml(ω), Ymr(ω), Ydl(ω) and Ydr(ω) (at S46).

The arithmetic processing module 2 calculates the impulse response Il(t) using the spectra Yml(ω) and X(ω) acquired in operation S45, and calculates the impulse response Ir(t) using the spectra Ymr(ω) and X(ω) (at S47). The arithmetic processing module 2 stores the impulse responses Il(t) and Ir(t) calculated in operation S47, the transform matrix Ts calculated in operation S46, and the information representing the ears position acquired in operation S43 in the transform matrix table 5*a* in a state of being associated with one another (at S48).

The arithmetic processing module 2 determines whether or not the process is completed for all positions where the dummy head is to be shifted (at S49). If determined the process is not completed (at S49: NO), the arithmetic processing module 2 returns the process to operation S41 to repeat the processes of steps S41 to S48. The arithmetic processing module 2, if determining the process is completed for all positions (at S49: YES), terminates the generating process of the transform matrix table 5*a* described above.

With the configuration described above, the car audio system 1 according to Embodiment 4 can store in the transform matrix table 5*a* with not only the transfer functions (impulse responses) of the sounds received by the error microphones 8*a* and 9*a*, and the transform matrix for transforming into the transfer functions at the listening points, but also the information of the ears positions of the dummy head at the time of acquiring each transfer function, in a state of being associated with one another.

Figure 15:
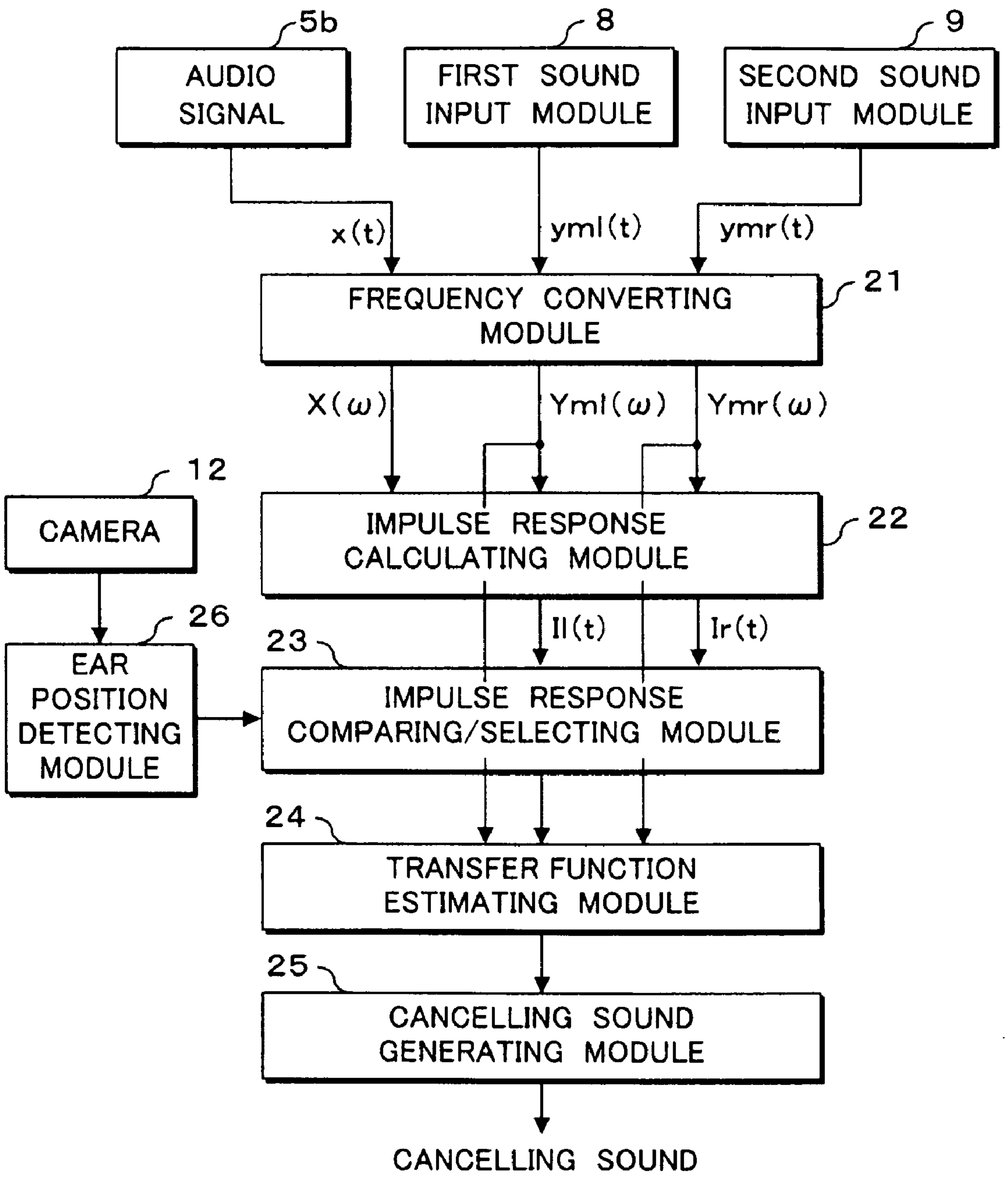
FIG. 15 is a functional block diagram illustrating an example of a functional configuration of the car audio system according to Embodiment 4.

Hereinafter, description will be given of the noise suppressing process using the transform matrix table 5*a* where the impulse responses of the sounds received by the error microphones 8*a* and 9*a*, the transform matrix, and the ears position information are registered therein which are associated with identification information as described above. Referring to FIG. 15, the arithmetic processing module 2 of Embodiment 4 has a function of the ears position detecting module 26 when conducting the noise suppressing process using the transform matrix table 5*a*, in addition to the configuration illustrated in FIG. 4. Incidentally, when the arithmetic processing module 2 conducts the noise suppressing process, the camera 12 captures an image of the face of the listener (driver), and the ears position detecting module 26 detects the position of the ears of the listener on the basis of image data obtained by the camera 12 capturing.

The impulse response comparing/selecting module 23 of Embodiment 4 compares each of the impulse responses Il(t) and Ir(t) calculated by the impulse response calculating module 22 with the impulse response registered in the transform matrix table 5*a*, as well as compares the ears position of the listener detected by the ears position detecting module 26 with the ears position information registered in the transform matrix table 5*a*. Then, the impulse response comparing/selecting module 23 selects from the transform matrix table 5*a* the identification number corresponding to the impulse response closest to each of the impulse responses Il(t) and Ir(t), or the identification number corresponding to the information of the ears position closest to the ears position of the listener, and notifies the transfer function estimating module 24 of the selected identification number.

Note that the configuration except for the impulse response comparing/selecting module 23 conducts a similar process to those described above in Embodiment 1; thus, description thereof is omitted.

With the configuration described above, the transfer functions at the ears positions of the listener can be estimated, on the basis of the transform matrix stored in the transform matrix table 5*a* corresponding to the impulse responses closest to the impulse responses of the sounds received by the error microphones 8*a* and 9*a*, or the transform matrix stored in the transform matrix table 5*a* corresponding to the information of the ears positions closest to the ears positions of the listener.

Hereinafter, description will be given of the noise suppressing process of the car audio system 1 according to Embodiment 4 on the basis of an operation chart. Note that the following process is executed by the arithmetic processing module 2 according to control program stored in the ROM 3 or the storage module 5 of the car audio system 1.

Figure 16:
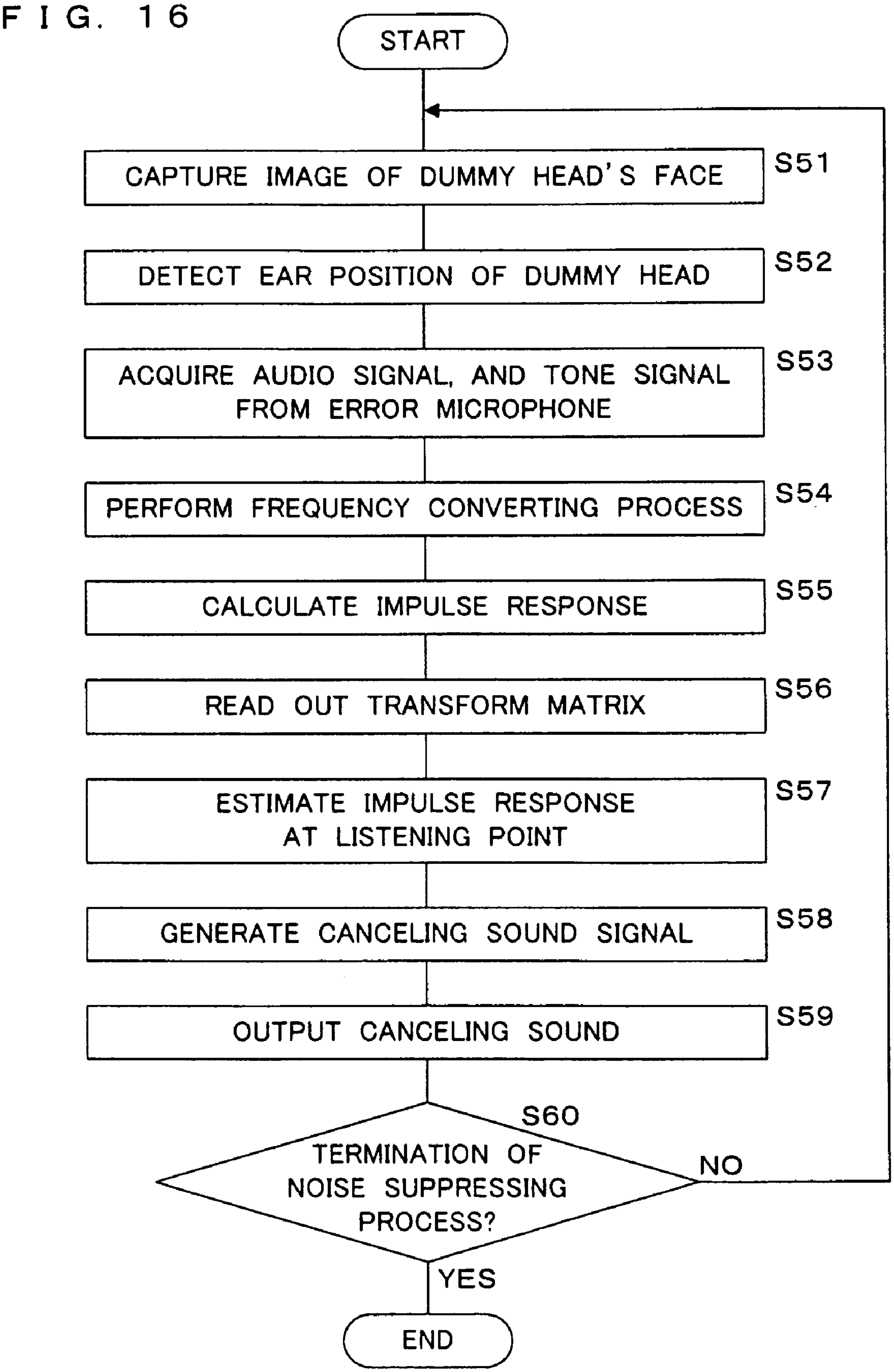
FIG. 16 is an operation chart illustrating an example of a procedure of a noise suppressing process of Embodiment 4.

Referring to FIG. 16, the arithmetic processing module 2 of the car audio system 1, for example, when outputting the audio signal 5*b* from the sound source loud speaker 6*a* is started, captures an image of the face of the listener by the camera 12 (at S51). The arithmetic processing module 2 (ears position detecting module 26) detects the ears position of the listener on the basis of the image data acquired from the camera 12 (at S52) to acquire the information representing the ears position.

The arithmetic processing module 2 acquires the audio signal 5*b* (x(t)) and the tone signals yml(t) and ymr(t) from the error microphones 8*a* and 9*a* (at S53). The arithmetic processing module 2 conducts the frequency conversion process for the audio signal 5*b* (x(t)), and the tone signals yml(t) and ymr(t) which are acquired (at S54) to obtain the spectra X(ω), Yml(ω) and Ymr(ω).

The arithmetic processing module 2 calculates the impulse response Il(t) using the spectra Yml(ω) and X(ω) acquired in operation S54, and calculates the impulse response Ir(t) using the spectra Ymr(ω) and X(ω) (at S55). The arithmetic processing module 2 reads out the optimum transform matrix Ts from the transform matrix table 5*a* on the basis of the calculated impulse responses Il(t) and Ir(t), and the ears position information detected in operation S52 (at S56).

The arithmetic processing module 2 estimates the impulse responses IFFT{aveYdl'(ω)/aveX(ω)} and IFFT{aveYdr'(ω)/aveX(ω)} at the listening points (ears positions of the listener) using the read out transform matrix Ts and the spectra Yml(ω) and Ymr(ω) acquired in operation S54 (at S57). The arithmetic processing module 2 generates such a canceling sound signal that it suppresses the noise from the sound source loud speaker 6*a* (noise source) at the ears positions of the listener on the basis of the estimated impulse responses at the listening points (at S58). The arithmetic processing module 2 outputs the canceling sound on the basis of the generated canceling sound signals via the canceling sound loud speaker 7*a* (at S59).

The arithmetic processing module 2 determines whether or not a termination of the noise suppressing process of the car audio system 1 is instructed (at S60). For example, if the engine of the vehicle is turned off, the arithmetic processing module 2 determines the termination or the noise suppressing process is instructed. The arithmetic processing module 2, if determining the termination of the noise suppressing process is not instructed (at S60: NO), returns the process to operation S51 to repeat the processes of steps S51 to S59. The arithmetic processing module 2, if determining the termination of the noise suppressing process is instructed (at S60: YES), terminates the noise suppressing process described above.

As described above, the car audio system 1 according to Embodiment 4 selects, on the basis of not only the transfer functions at the error microphones 8*a* and 9*a* but also the ears positions of the listener, the optimum transform matrix from the transform matrix table 5*a*. Therefore, the excellent noise suppressing process is enabled with the canceling sound signals generated on the basis of the optimum transform matrix.

The car audio system 1 according to Embodiment 4 described above has the configuration where are stored in the transform matrix table 5*a* not only the transfer functions and the transform matrix, but also the ears position information of the dummy head. However, the configuration is not limited to this, and may be, for example, a distance between two ears of the dummy head and hairstyle information of the dummy head are stored in the transform matrix table 5*a* instead of the ears position information of the dummy head. In a case of conducting the noise suppressing process using the transform matrix table 5*a* like this, the arithmetic processing module 2 may detect the distance between two ears or the hairstyle of the listener to select the transform matrix corresponding to the detected distance between the ears or hairstyle on the basis of the image data obtained by the camera 12 capturing.

Embodiment 5

Hereinafter, a car audio system according to Embodiment 5 is described. Incidentally, the car audio system according to Embodiment 5 can be implemented with a configuration including a similar configuration to the car audio system 1 according to Embodiment 4 described above. Therefore, the same reference numerals are attached in the similar configuration, and the description thereof will be omitted.

The car audio system 1 according to Embodiment 4 described above has the configuration where the identification number, the two transfer functions Il(t) and Ir(t), the transformation coefficient Ts, and the ears position information of the dummy head are registered in the transform matrix table 5*a* in a state of being associated with one another, in plural numbers. The car audio system 1 of Embodiment 5 has a configuration where registered the transform matrix table 5*a* are, an ambient temperature at the time of calculating each of the transfer functions Il(t) and Ir(t), and the transformation coefficient Ts, in instead of the ears position information of the dummy head.

The car audio system 1 according to Embodiment 5 is provided with a thermometer (temperature measuring module) 13 for measuring such as the temperature inside the vehicle at a given position and the ambient temperature, and the thermometer 13 is couple to the body of the car audio system 1 via a cable.

Figure 17:
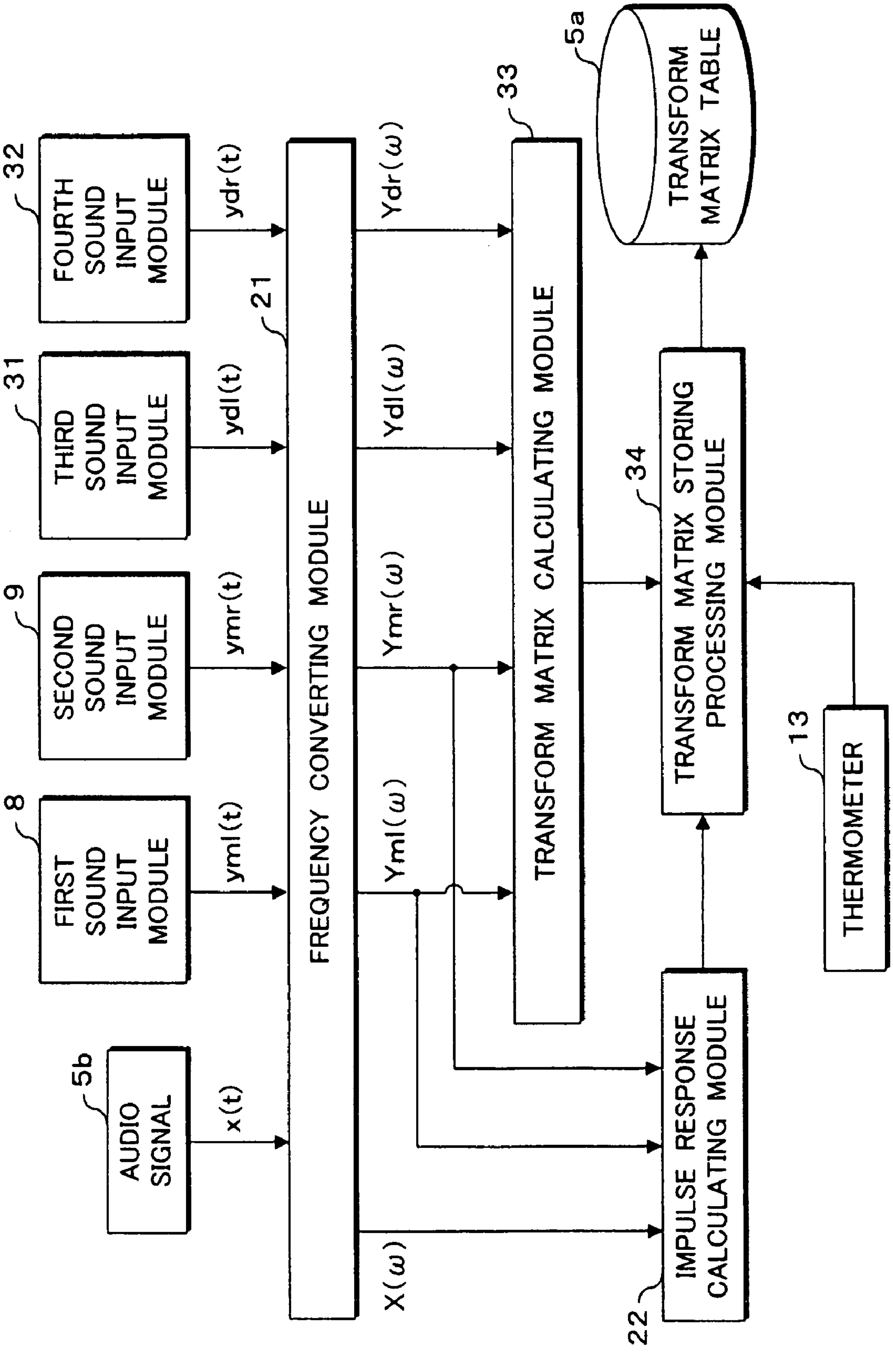
FIG. 17 is a functional block diagram illustrating an example of a functional configuration of a car audio system according to Embodiment 5.

Referring to FIG. 17, the transform matrix storing processing module 34 of Embodiment 5, when conducting the generating process of the transform matrix table 5*a*, acquires a temperature measured by the thermometer 13 instead of the ears position detecting module 26 illustrated in FIG. 13.

The transform matrix storing processing module 34 of Embodiment 5 attaches the identification number to the impulse responses Il(t) and Ir(t) acquired from the impulse response calculating module 22, the transform matrix Ts acquired from the transform matrix calculating module 33, and the temperature from the thermometer 13, and stores the identification number, the impulse responses Il(t) and Ir(t), the transform matrix Ts, and the temperature in the transform matrix table 5*a* in a state of being associated with one another.

Incidentally, a process of generating the transform matrix table 5*a* in the car audio system 1 according to Embodiment 5 is similar to that of Embodiment 4 described above; thus, the description thereof is omitted. Note that the arithmetic processing module 2 of Embodiment 5 conducts a process of measuring the temperature with the thermometer 13 instead of the steps S42 and S43 of the operation chart illustrated in FIG. 14.

With the configuration described above, the car audio system 1 according to Embodiment 5 can store the ambient temperature at the time of each transfer function being acquired in the transform matrix table 5*a* in a state of being associated therewith, in addition to the transform matrix for transforming into the transfer functions (impulse responses) of the sounds received by the error microphones 8*a* and 9*a*, and the transfer functions at the listening points.

Figure 18:
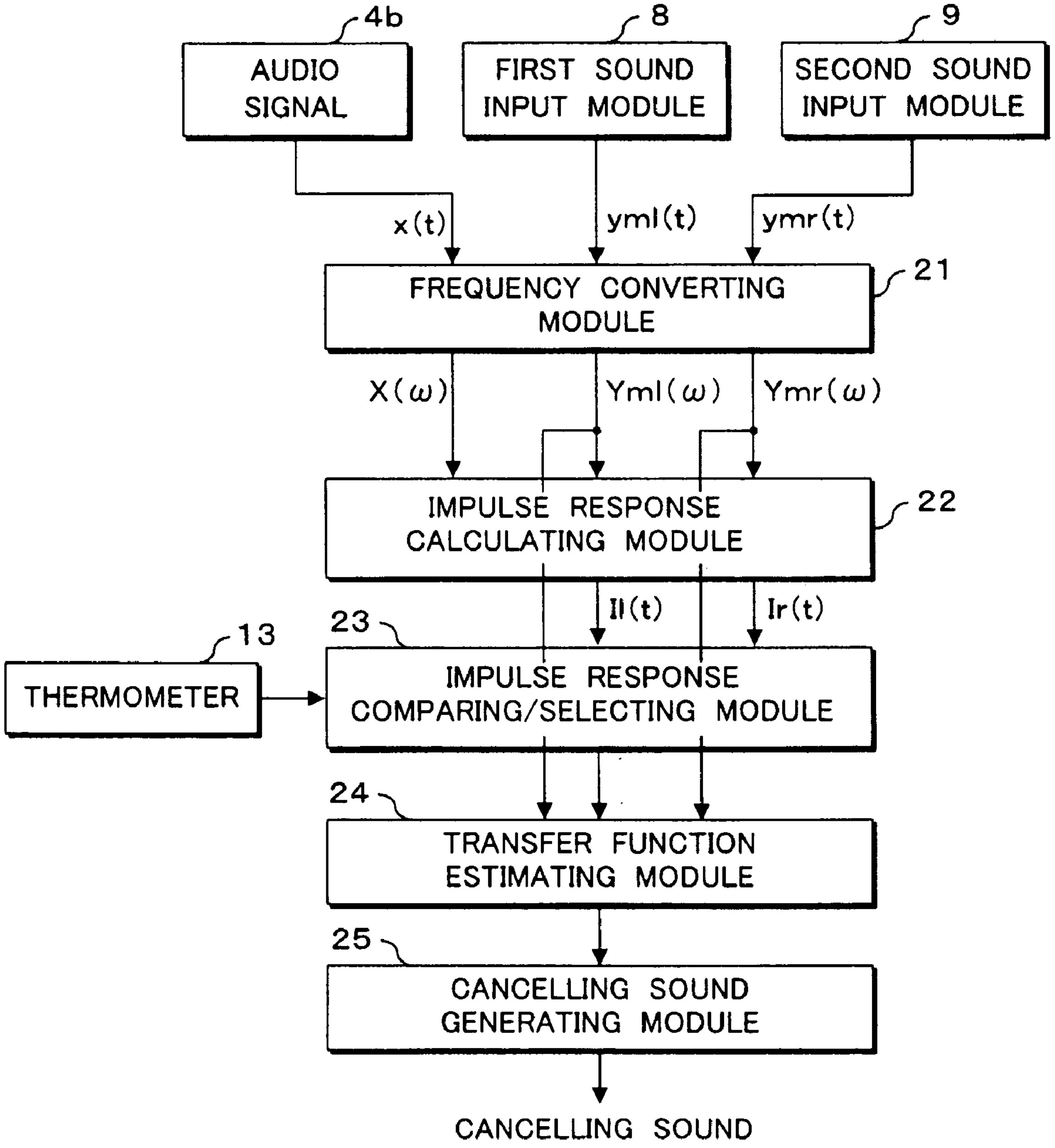
FIG. 18 is a functional block diagram illustrating an example of a functional configuration of the car audio system according to Embodiment 5.
Figure 19:
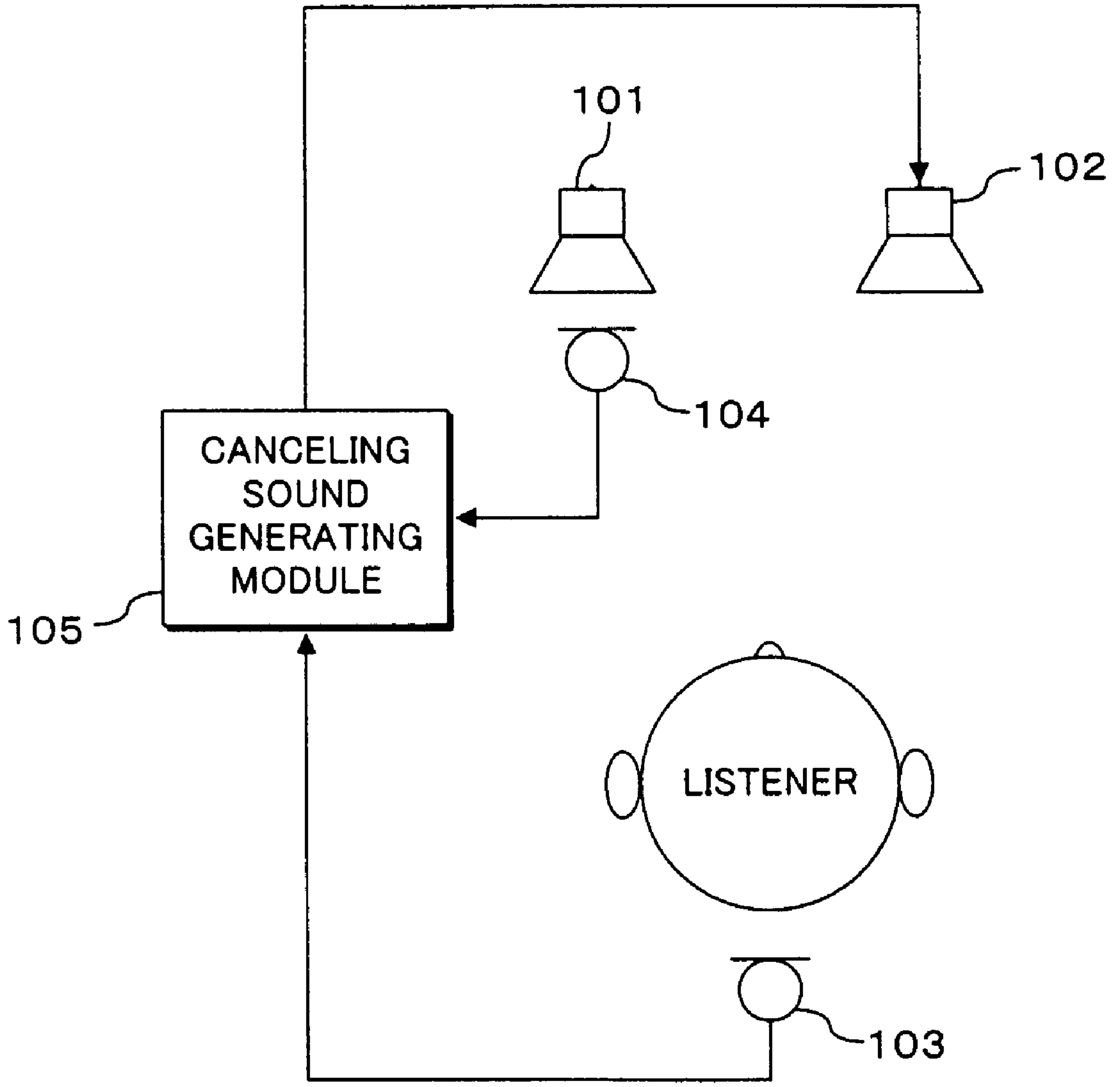
FIG. 19 RELATED ART
FIG. 19 is a schematic view of a configuration example of a noise suppressing apparatus of related art.

Hereinafter, description will be given of the noise suppressing process using the transform matrix table 5*a* where, as described above, registered are the impulse responses of the sounds received by the error microphones 8*a* and 9*a*, the transform matrix, and the temperature with the identification information associated therewith. Referring to FIG. 18, the impulse response comparing/selecting module 23 of Embodiment 5, when conducting the noise suppressing process using the transform matrix table 5*a*, acquires the temperature measured by the thermometer 13 instead of the ears position detecting module 26 illustrated in FIG. 15.

The impulse response comparing/selecting module 23 of Embodiment 5 compares each of the impulse responses Il(t) and Ir(t) calculated by the impulse response calculating module 22 with the impulse responses registered in the transform matrix table 5*a*, as well as compares the temperature measured by the thermometer 13 with the temperatures registered in the transform matrix table 5*a*. Then, the impulse response comparing/selecting module 23 selects from the transform matrix table 5*a* the identification number corresponding to the impulse response closest to each of the impulse responses Il(t) and Ir(t) or the identification number corresponding to the temperature closest to the measured temperature, and notifies the transfer function estimating module 24 of the selected identification number.

Incidentally, the noise suppressing process of Embodiment 5 is a similar to the process in Embodiment 4 described above; thus, the description thereof is omitted. Note that the arithmetic processing module 2 of Embodiment 5 conducts the process of measuring the temperature by the thermometer 13, instead of steps S51 and S52 of the operation chart illustrated in FIG. 16.

As described above, the car audio system 1 of Embodiment 5 selects an appropriate transform matrix from the transform matrix table 5*a* on the basis of not only the transfer functions at the error microphones 8*a* and 9*a* but also the ambient temperature. Therefore, the excellent noise suppressing process is enabled with the canceling sound signals generated on the basis of the optimum transform matrix.

Embodiments 1 to 5 described above are described using, as an example, the configuration where the transfer function estimating device, transfer function estimating method and computer program disclosed in the present application are applied to the car audio system 1, but are not limited to such a configuration. The transfer function estimating device disclosed in the present application can accurately estimate the transfer functions of the sounds at the position which is not an actual observation position; therefore, can be applied to various devices which conducts various processes using such transfer functions.

The transfer function estimating device disclosed in the present application stores in the storage module the first transfer function of the sounds propagated from a given sound source to the sound receiving module, the transformation coefficient for transforming the first transfer function into a given second transfer function in a state being associated with each other. The transfer function estimating device disclosed in the present application reads out from the storage module the transformation coefficient corresponding to the first transfer function including the highest cross-correlation value between the transfer functions of the sounds received by the sound receiving module and the first transfer function stored in the storage module to estimate the second transfer function corresponding to the found transfer functions using the read out transformation coefficient. Therefore, the desired second transfer function can be estimated, on the basis of the transfer functions of the sounds received by the sound receiving module and the optimum transformation coefficient for the transfer functions.

The transfer function estimating method disclosed in the present application estimates the second transfer function corresponding to the transfer functions of the sounds received by the sound receiving module, using the transformation coefficient specified on the basis of the transfer functions the sounds received by the sound receiving module. Therefore, the desired second transfer function can be estimated on the basis of the transfer functions of the sounds received by the sound receiving module and the transformation coefficient optimum for the transfer functions.

The computer program disclosed in the present application estimates the second transfer function corresponding to the found transfer functions using the transformation coefficient specified on the basis of the transfer functions of the tone signals obtained by receiving the sound. Therefore, the desired second transfer function can be estimated on the basis of the transfer functions of the sounds received by the sound receiving module and the transformation coefficient optimum for the transfer functions.

The transfer function estimating device and the transfer function estimating method disclosed in the present application can estimate accurately the desired second transfer function from the transfer functions of sounds received by the sound receiving module, using the transformation coefficient optimum for the transfer functions of the sounds received by the sound receiving module. Therefore, even in cases where the sound receiving module is provided at the position apart from the listening point, and the position of the listening point is changed, the optimum second transfer function between a given sound source and the listening point can be accurately estimated. Further, with the computer programs disclosed in the present application, the transfer function estimating device including the configuration described above can be implemented by a computer.

As this description may be embodied in several forms without departing from the spirit of essential characteristics thereof, the present embodiment is therefore illustrative and not restrictive, since the scope of the description is defined by the appended claims rather than by description preceding them, and all changes that fall within metes and bounds of the claims, or equivalence of such metes and bounds thereof are therefore intended to be embraced by the claims.

What is claimed is:

1. A transfer function estimating device for estimating a transfer function of a sound, comprising:

a sound receiving module receiving a sound from a given sound source and converting the sound into a tone signal;

a storage module storing first transfer functions of the sound propagating from the given sound source to the sound receiving module and transformation coefficients for converting the first transfer functions into given second transfer functions so as to associate with each other;

a reference tone signal acquiring module acquiring a reference tone signal of the sound source;

an acquiring module acquiring a transfer function of the sound received by the sound receiving module on the basis of the tone signal and the reference tone signal;

a specifying module acquiring a cross-correlation value between the transfer function acquired by the acquiring module and each of the first transfer functions stored in the storage module, and specifying the first transfer function indicating the highest cross-correlation value;

a read-out module reading out the transformation coefficient corresponding to the first transfer function specified by the specifying module from the storage module; and an estimating module estimating the second transfer function corresponding to the transfer function acquired by the acquiring module using the transformation coefficient read out by the read-out module.

2. The transfer function estimating device according to claim 1, wherein the acquiring module acquires the transfer function of the sound received by the sound receiving module for every given interval on the basis of the tone signal and the reference tone signal, the transfer function estimating device further comprises:

a degree of similarity acquiring module acquiring a degree of similarity between the transfer function acquired by the acquiring module and the transfer function already acquired; and a determination module determining whether or not the degree of similarity acquired by the degree of similarity acquiring module is equal to or less than a given value, and the specifying module, if the determination module determines that the degree of similarity is equal to or less than the given value, acquires again the cross-correlation value between the transfer function acquired by the acquiring module and each of the first transfer functions stored in the storage module, and newly specifies the first transfer function including the highest cross-correlation value.

3. The transfer function estimating device according to claim 1, further comprising:

a camera acquiring an image of a face of a listener; and a position detecting module detecting a position of a listening point by extracting a position of a ear of the listener from the acquired image and generates position information concerning the position, wherein the storage module stores the position information so as to associate with the first transfer functions and the transformation coefficients, and the read-out module reads out from the storage module the transformation coefficient corresponding to both the position information detected and generated by the position detecting module and the first transfer function specified by the specifying module.

4. The transfer function estimating device according to claim 2, further comprising:

a camera acquiring an image of a face of a listener; and a position detecting module detecting a position of a listening point by extracting a position of a ear of the listener from the acquired image and generates position information concerning the position, wherein the storage module stores the position information so as to associate with the first transfer functions and the transformation coefficients, and the read-out module reads out from the storage module the transformation coefficient corresponding to both the position information detected and generated by the position detecting module and the first transfer function specified by the specifying module.

5. The transfer function estimating device according to claim 1, further comprising:

a camera acquiring an image of a face of a listener; and a distance detecting module detecting a distance between two listening points by extracting positions of ears of the listener from the acquired image and generating distance information concerning the distance, wherein the storage module stores the distance information so as to associate with the first transfer functions and the transformation coefficients, the read-out module reads out from the storage module the transformation coefficient corresponding to both the distance information detected and generated by the distance detecting module and the first transfer function specified by the specifying module.

6. The transfer function estimating device according to claim 2, further comprising:

a camera acquiring an image of a face of a listener; and a distance detecting module detecting distance information between two listening points by extracting positions of ears of the listener from the acquired image, wherein the storage module stores the first transfer functions and the transformation coefficients so as to associate with the distance information, the read-out module reads out from the storage module the transformation coefficient corresponding to both the distance information detected by the distance detecting module and the first transfer function specified by the specifying module.

7. The transfer function estimating device according to claim 1, further comprising:

a thermometer measuring an ambient temperature and generating temperature information concerning the ambient temperature, wherein the storage module stores the temperature information so as to associate the first transfer functions and the transformation coefficients, and the read-out module reads out from the storage module the transformation coefficient corresponding to both the temperature information measured and generated by the temperature measuring module and the first transfer function specified by the specifying module.

8. The transfer function estimating device according to claim 2, further comprising:

a thermometer measuring an ambient temperature and generating temperature information concerning the ambient temperature, wherein the storage module stores the temperature information so as to associate the first transfer functions and the transformation coefficients, and the read-out module reads out from the storage module the transformation coefficient corresponding to both the temperature information measured and generated by the temperature measuring module and the first transfer function specified by the specifying module.

9. The transfer function estimating device according to claim 1, further comprising:

a tone signal acquiring module receiving a sound on the basis of a given tone signal at a plurality of positions and converting the sound into corresponding tone signals respectively corresponding to the plurality of positions;

a transfer function acquiring module acquiring the first transfer functions of the sound received by the sound receiving module on the basis of both the given tone signal and the tone signals converted by the sound receiving module receiving the sound on the basis of the given tone signal;

a transformation coefficient acquiring module acquiring transformation coefficients for converting the tone signal converted by the sound receiving module receiving the sound on the basis of the given tone signal into the tone signals converted by the tone signal acquiring module receiving the sound on the basis of the given tone signal; and a storage control module storing in the storage module the first transfer functions acquired by the transfer function acquiring module so as to associate with the transformation coefficients acquired by the transformation coefficient acquiring module.

10. The transfer function estimating device according to claim 2, further comprising:

a tone signal acquiring module receiving a sound on the basis of a given tone signal at a plurality of positions and converting the sound into corresponding tone signals respectively corresponding to the plurality of positions;

a transfer function acquiring module acquiring the first transfer functions of the sound received by the sound receiving module on the basis of both the given tone signal and the tone signals converted by the sound receiving module receiving the sound on the basis of the given tone signal;

a transformation coefficient acquiring module acquiring transformation coefficients for converting the tone signal converted by the sound receiving module receiving the sound on the basis of the given tone signal into the tone signals converted by the tone signal acquiring module receiving the sound on the basis of the given tone signal; and a storage control module storing in the storage module the first transfer functions acquired by the transfer function acquiring module so as to associate with the transformation coefficients acquired by the transformation coefficient acquiring module.

11. The transfer function estimating device according to claim 9, wherein the tone signal acquiring module includes a plurality of tone signal acquiring modules, the transfer function estimating device further comprises a changing module for changing an arrangement interval of the tone signal acquiring modules, and the transformation coefficient acquiring module obtains the transformation coefficients for converting the tone signal converted by the sound receiving module receiving the sound on the basis of the given tone signal into the tone signals converted by the tone signal acquiring module receiving the sound on the basis of the given tone signal, the arrangement interval of the tone signal acquiring modules being changed by the changing module.

12. The transfer function estimating device according to claim 10, wherein the tone signal acquiring module includes a plurality of tone signal acquiring modules, the transfer function estimating device further comprises a changing module for changing an arrangement interval of the tone signal acquiring modules, and the transformation coefficient acquiring module obtains the transformation coefficients for converting the tone signal converted by the sound receiving module receiving the sound on the basis of the given tone signal into the tone signals converted by the tone signal acquiring module receiving the sound on the basis of the given tone signal, the arrangement interval of the tone signal acquiring modules being changed by the changing module.

13. The transfer function estimating device according to claim 9, wherein the transformation coefficient acquiring module obtains the transformation coefficients when a signal value of the tone signal converted by the sound receiving module receiving the sound on the basis of the given tone signal and/or a signal value of the tone signal converted by the tone signal acquiring module receiving the sound on the basis of the given tone signal is equal to or more than a given value.

14. The transfer function estimating device according to claim 10, wherein the transformation coefficient acquiring module obtains the transformation coefficients when a signal value of the tone signal converted by the sound receiving module receiving the sound on the basis of the given tone signal and/or a signal value of the tone signal converted by the tone signal acquiring module receiving the sound on the basis of the given tone signal is equal to or more than a given value.

15. The transfer function estimating device according to claim 11, wherein the transformation coefficient acquiring module obtains the transformation coefficients when a signal value of the tone signal converted by the sound receiving module receiving the sound on the basis of the given tone signal and/or a signal value of the tone signal converted by the tone signal acquiring module receiving the sound on the basis of the given tone signal is equal to or more than a given value.

16. The transfer function estimating device according to claim 12, wherein the transformation coefficient acquiring module obtains the transformation coefficients when a signal value of the tone signal converted by the sound receiving module receiving the sound on the basis of the given tone signal and/or a signal value of the tone signal converted by the tone signal acquiring module receiving the sound on the basis of the given tone signal is equal to or more than a given value.

17. A noise suppressing apparatus comprising:

a transfer function estimating device including:

a sound receiving module receiving a sound from a given sound source and converting the sound into a tone signal;

a storage module storing first transfer functions of the sound propagating from the given sound source to the sound receiving module and transformation coefficients for converting the first transfer functions into given second transfer functions therein so as to associate with each other;

a reference tone signal acquiring module acquiring a reference tone signal of the sound source;

an acquiring module acquiring a transfer function of the sound including been received by the sound receiving module on the basis of the tone signal and the reference tone signal;

a specifying module acquiring a cross-correlation value between the transfer function acquired by the acquiring module and each of the first transfer functions stored in the storage module, and specifying the first transfer function including the highest cross-correlation value;

a read-out module reading out the transformation coefficient corresponding to the first transfer function specified by the specifying module from the storage module; and an estimating module estimating the second transfer function corresponding to the transfer function acquired by the acquiring module using the transformation coefficient read out by the read-out module;

a generating module generating a canceling tone signal for suppressing a noise component included in the sound from the given sound source on the basis of the second transfer functions estimated by the transfer function estimating device; and an output module outputting a canceling sound on the basis of the generated canceling tone signal.

18. A transfer function estimating method for estimating a transfer function of a sound using a transfer function estimating device which includes:

a sound receiving module receiving a sound from a given sound source and converting the sound into a tone signal;

a storage module storing first transfer functions of the sound propagating from the given sound source to the sound receiving module and transformation coefficients for converting the first transfer functions into given second transfer functions so as to associate with each other, the method comprising:

acquiring a reference tone signal of the sound source;

acquiring a transfer function of the sound received by the sound receiving module on the basis of the tone signal and the reference tone signal;

acquiring a cross-correlation value between the acquired transfer function and each of the first transfer functions stored in the storage module, and specifying the first transfer function including the highest cross-correlation value;

reading out the transformation coefficient corresponding to the specified first transfer function from the storage module; and estimating the second transfer function corresponding to the acquired transfer function using the read out transformation coefficient.

19. A computer-readable recording medium which stores a computer-executable program for causing a computer to estimate a transfer function of a sound, the computer including: a sound receiving module for receiving the sound from a given sound source and converting the sound into a tone signal; and a storage module storing first transfer functions of the sound propagating from the given sound source to the sound receiving module and transformation coefficients for converting the first transfer functions into given second transfer functions so as to associate with each other, the program making the computer execute:

acquiring a reference tone signal of the sound source;

acquiring a transfer function of the sound received by the sound receiving module on the basis of the tone signal and the reference tone signal;

acquiring a cross-correlation value between the acquired transfer function and each of the first transfer functions stored in the storage module, and specifying the first transfer function including the highest cross-correlation value;

reading out the transformation coefficient corresponding to the specified first transfer function from the storage module; and estimating the second transfer function corresponding to the acquired transfer function using the read out transformation coefficient.

20. A transfer function estimating device for estimating a transfer function of a sound, comprising:

sound receiving means for receiving a sound from a given sound source and converting the sound into a tone signal;

storage means for storing first transfer functions of the sound propagating from the given sound source to the sound receiving module and transformation coefficients for converting the first transfer functions into given second transfer functions so as to associate with each other;

reference tone signal acquiring means for acquiring a reference tone signal of the sound source;

acquiring means for acquiring a transfer function of the sound including been received by the sound receiving means on the basis of the tone signal and the reference tone signal;

specifying means for acquiring a cross-correlation value between the transfer function acquired by the acquiring means and each of the first transfer functions stored in the storage means, and specifying the first transfer function including the highest cross-correlation value;

read-out means for reading out the transformation coefficient corresponding to the first transfer function specified by the specifying means from the storage means; and estimating means for estimating the second transfer function corresponding to the transfer function acquired by the acquiring means using the transformation coefficient read out by the read-out means.

* * * * *